US009486128B1

(12) United States Patent
Hannaford et al.

(10) Patent No.: US 9,486,128 B1
(45) Date of Patent: Nov. 8, 2016

(54) SENSING AND AVOIDING SURGICAL EQUIPMENT

(71) Applicant: Verily Life Sciences LLC, Mountain View, CA (US)

(72) Inventors: Blake Hannaford, Seattle, WA (US); Eden Rephaeli, Menlo Park, CA (US); Chia-Jean Wang, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 14/506,335

(22) Filed: Oct. 3, 2014

(51) Int. Cl.
*A61B 1/06* (2006.01)
*A61B 5/00* (2006.01)

(52) U.S. Cl.
CPC ............. *A61B 1/063* (2013.01); *A61B 5/0075* (2013.01)

(58) Field of Classification Search
CPC ..... A61B 5/06; A61B 5/0071; A61B 5/0075
USPC .................................. 600/473, 314
See application file for complete search history.

(56) References Cited

U.S. PATENT DOCUMENTS

| 5,649,546 | A * | 7/1997 | Steinbeck | G01V 3/102 340/551 |
| 6,292,695 | B1 * | 9/2001 | Webster, Jr. | A61N 1/0563 607/113 |
| 6,370,411 | B1 * | 4/2002 | Osadchy | A61B 5/06 600/372 |
| 6,437,770 | B1 * | 8/2002 | Venema | G06F 3/011 345/156 |
| 6,594,518 | B1 | 7/2003 | Benaron et al. | |
| 7,806,122 | B2 * | 10/2010 | Hoendervoogt | A61M 5/14276 128/899 |
| 8,229,548 | B2 * | 7/2012 | Frangioni | A61B 1/00186 600/473 |
| 8,702,626 | B1 * | 4/2014 | Kim | A61M 25/09041 600/424 |

(Continued)

*Primary Examiner* — Ellen C Hammond
*Assistant Examiner* — Stuart S Bray
(74) *Attorney, Agent, or Firm* — McDonnell Boehnen Hulbert & Berghoff LLP

(57) ABSTRACT

A surgical imaging system includes a light source configured to illuminate a portion of a surgical environment and a light sensor configured to receive light from the illuminated portion in response to the illumination. The surgical imaging system determines spectrographic content of the received light and uses the determined spectrographic content to identify the illuminated portion of the surgical environment; for example, to determine that the portion contains a surgical instrument, a foreign body, a suture, a particular type of tissue, a blood vessel, and/or a fluorescent marker. This identification of the illuminated portion of the surgical environment could be used to implement a surgical intervention. For example, a surgical laser could be operated, based on such generated identification information, to ablate cancerous tissue in the surgical environment that is marked with a fluorophore while avoiding ablating any sutures or surgical instruments disposed in the surgical environment.

13 Claims, 10 Drawing Sheets

(56) References Cited

U.S. PATENT DOCUMENTS

| | | | |
|---|---|---|---|
| 2001/0027273 A1* | 10/2001 | Flock | A61B 5/0059 600/473 |
| 2002/0038121 A1* | 3/2002 | Rozenberg | A61B 5/06 606/15 |
| 2002/0049386 A1* | 4/2002 | Yang | A61B 5/0059 600/476 |
| 2002/0049389 A1* | 4/2002 | Abreu | A61B 3/1241 600/558 |
| 2003/0100824 A1* | 5/2003 | Warren | A61B 5/0066 600/407 |
| 2005/0054910 A1 | 3/2005 | Tremblay et al. | |
| 2007/0055128 A1* | 3/2007 | Glossop | A61B 1/005 600/407 |
| 2007/0161922 A1* | 7/2007 | Dekel | A61B 5/0091 600/549 |
| 2007/0213618 A1* | 9/2007 | Li | A61B 1/00096 600/476 |
| 2007/0232883 A1* | 10/2007 | Ilegbusi | A61B 1/00082 600/407 |
| 2008/0291463 A1* | 11/2008 | Milner | A61B 1/00096 356/491 |
| 2009/0281412 A1* | 11/2009 | Boyden | A61B 5/0059 600/407 |
| 2009/0318802 A1* | 12/2009 | Boyden | A61B 5/02007 600/437 |
| 2010/0042005 A1* | 2/2010 | Bigio | G01N 21/59 600/476 |
| 2010/0055666 A1* | 3/2010 | Wimberger-Friedl | G01N 21/6454 435/4 |
| 2010/0145200 A1* | 6/2010 | Mahadevan-Jansen | A61B 5/0091 600/476 |
| 2010/0160789 A1* | 6/2010 | Dilworth | A61B 3/0025 600/476 |
| 2010/0168586 A1* | 7/2010 | Hillman | G02B 23/2476 600/476 |
| 2010/0179436 A1* | 7/2010 | Sarfaty | A61B 5/0075 600/476 |
| 2010/0222670 A1* | 9/2010 | Demierre | A61B 1/00016 600/424 |
| 2010/0234762 A1 | 9/2010 | Pond et al. | |
| 2011/0020779 A1* | 1/2011 | Hannaford | G06F 19/327 434/262 |
| 2011/0117025 A1* | 5/2011 | Dacosta | A61B 5/0059 424/9.6 |
| 2012/0123205 A1* | 5/2012 | Nie | A61B 1/00174 600/109 |
| 2012/0326055 A1* | 12/2012 | Wilson | A61B 5/0059 250/459.1 |
| 2013/0035569 A1* | 2/2013 | Heanue | G01J 3/02 600/322 |
| 2013/0162796 A1* | 6/2013 | Bharara | A61B 5/0077 348/77 |
| 2013/0274596 A1 | 10/2013 | Azizian et al. | |
| 2014/0135816 A1* | 5/2014 | Hyde | A61F 2/01 606/200 |
| 2014/0148882 A1* | 5/2014 | Dae | A61F 7/0085 607/106 |
| 2014/0303606 A1 | 10/2014 | Garner-Richards et al. | |
| 2014/0313172 A1* | 10/2014 | Moe | A61B 17/00 345/184 |
| 2014/0364743 A1* | 12/2014 | Godavarty | A61B 5/0071 600/473 |
| 2015/0297309 A1* | 10/2015 | Bly | G06F 19/3437 700/98 |

* cited by examiner

SENSING AND AVOIDING SURGICAL EQUIPMENT

BACKGROUND

Unless otherwise indicated herein, the materials described in this section are not prior art to the claims in this application and are not admitted to be prior art by inclusion in this section.

A variety of methods exist to generate information about biological tissues. Such methods can include exposing the biological tissues to an energy or field (e.g., an electric field, a magnetic field, an electromagnetic field, a light, an acoustic energy) and detecting a response of the biological tissues (e.g., a modification of the energy, and/or the emission of a second energy) that is related to one or more properties of the biological tissues. Properties of the biological tissues could include a type and/or distribution of cells and/or tissues within the biological tissues, a health or disease state of the biological tissues, the presence of a fluorophore or other contrast agent in the biological tissues, or some other information about the biological tissues. Such measured properties could be related to a health or medical condition of a human or animal containing the biological tissues and/or from which the biological tissues are derived.

In some examples, information about biological tissues could be generated to guide a surgical intervention related to the biological tissues. For example, the presence, location, extent, or other information about cancerous cells in a biological tissue could be determined and a surgical intervention (e.g., a removal or destruction of the cancerous cells, a placement of a drug-eluting device or other artifact within a mass of the cancerous cells) could be performed based on the determined information. In some examples, such information is generated before a surgical intervention (e.g., by a pre-surgical MRI, CT, or other type of scan or imaging) and used to inform a surgeon's actions during the surgical intervention.

SUMMARY

Some embodiments of the present disclosure provide a method including: (i) illuminating, by a light source, a portion of a surgical environment, wherein the surgical environment comprises tissue subject to a surgical intervention involving one or more surgical instruments (ii) receiving light from the illuminated portion of the surgical environment; (iii) determining a spectrographic content of the received light; and (iv) identifying at least one of a portion of the tissue or a portion of a foreign body in the illuminated portion of the surgical environment based on the spectrographic content of the received light.

Some embodiments of the present disclosure provide a system including: (i) a light source configured to illuminate a portion of a surgical environment, wherein the surgical environment comprises a tissue subject to a surgical intervention involving one or more surgical instruments; (ii) a detector configured to detect a spectrographic content of light received from the illuminated portion of the surgical environment; and (iii) a controller operatively coupled to the light source, wherein the controller includes a computing device programmed to perform operations comprising: (a) controlling the light source to illuminate the portion of the surgical environment; (b) controlling the detector to obtain the spectrographic content of the light received from the illuminated portion of the surgical environment; and (c) identifying at least one of a portion of the tissue or a portion of a foreign body in the illuminated portion of the surgical environment based on the spectrographic content of the received light.

Some embodiments of the present disclosure provide a system including: (i) means for illuminating a portion of a surgical environment, wherein the surgical environment comprises a tissue subject to a surgical intervention involving one or more surgical instruments; (ii) means for detecting a spectrographic content of light received from the illuminated portion of the surgical environment; and (iii) means for controlling the light source and the detector and configured to perform operations comprising: (a) controlling the means for illuminating the portion of the surgical environment to illuminate the portion of the surgical environment; (b) controlling the means for detecting the spectrographic content of light received from the illuminated portion of the surgical environment to obtain the spectrographic content of the light received from the illuminated portion of the surgical environment; and (c) identifying at least one of a portion of the tissue or a portion of a foreign body in the illuminated portion of the surgical environment based on the spectrographic content of the received light.

These as well as other aspects, advantages, and alternatives, will become apparent to those of ordinary skill in the art by reading the following detailed description, with reference where appropriate to the accompanying drawings.

DETAILED DESCRIPTION

Figure 1:
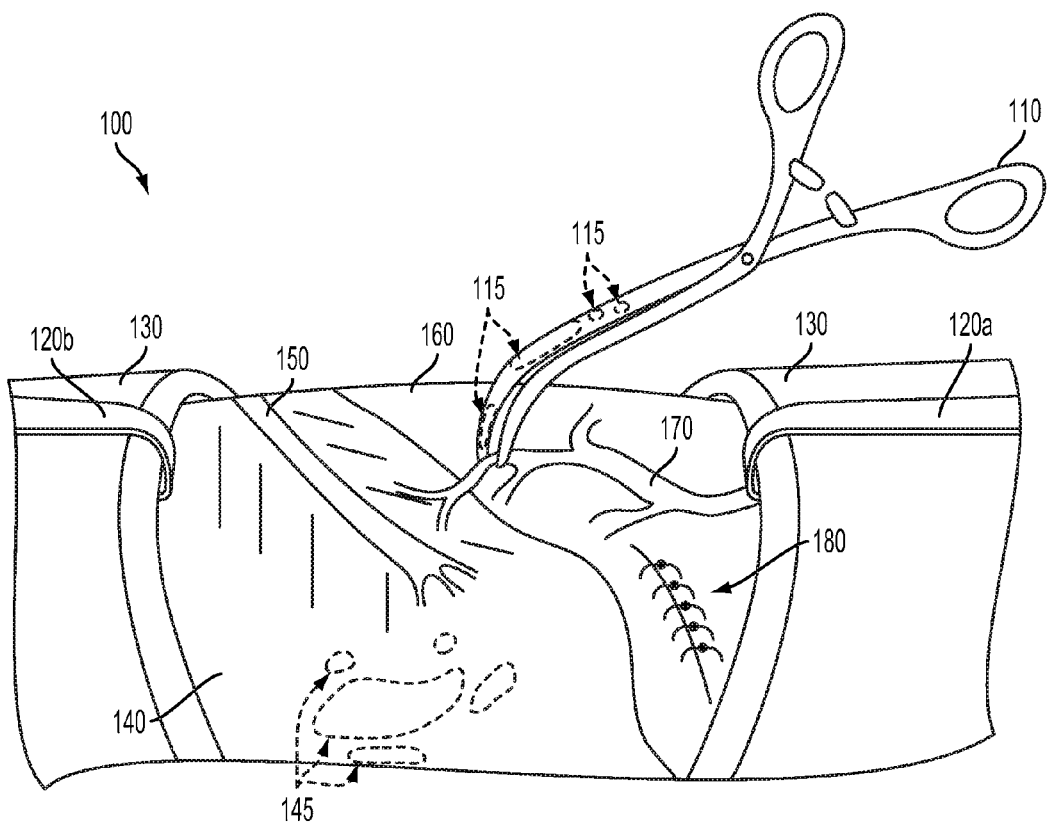
FIG. 1 illustrates an example surgical environment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body and/or tissues thereof, it is contemplated that the disclosed methods, systems and devices may be used in any environment where spectrographic imaging and/or identification of tissues or other objects or elements of an environment is desired. The environment may be any living or non-living body or a portion thereof, a work piece, an implantable device, etc. Moreover, while the present disclosure describes embodiments for use in vivo, one of skill in the art will also recognize that in vitro applications are possible as well. Accordingly, the environment may also include a test tube or other vessel for holding a fluid, a transplant tissue, and/or a stereotaxically or otherwise immobilized tissue.

I. Overview

A variety of information about tissues or other contents of a surgical environment (i.e., of a region containing tissue(s) of a human or animal body subject to some surgical intervention) could be determined based on spectrographic or other optical information about the contents of the surgical field. That is, spectrographic information about a particular portion or region of tissue within the surgical environment could be used to determine a tissue type, a disease state (e.g., a presence of cancer cells), the presence of a marker or fluorophore, a health state (e.g., a degree of perfusion), or some other information about the portion or region of tissue. Additionally or alternatively, such spectrographic information could be used to determine that a particular portion or region of the surgical environment contains a surgical instrument, suture, drape, staple, stent, or other artificial device or foreign body. Such information could be used to guide and/or plan a surgical intervention, to image tissue(s) of a human or animal body, to determine the effect of a surgical intervention (e.g., to determine a degree of ablation, cautery, debridement, or other surgical processes), or to enable some other applications.

Spectrographic information (or content) could include any information about the dependence of the absorbance, reflectance, excitation, emission, or some other interaction of a particular portion of a surgical environment with light applied to the portion (e.g., visible, infrared, or ultraviolet light) on the wavelength of the applied and/or emitted light. That is, spectrographic information could include one or more of an absorbance spectrum, a reflectance spectrum, an excitation spectrum, an emission spectrum, or some other spectrum detected and/or determined for a plurality of wavelengths. For example, spectrographic information could include a spectrum of light (e.g., a plurality of detected amplitudes corresponding to the amplitudes of light received in a plurality of respective ranges of wavelengths) emitted from a portion of the surgical environment in response to illumination of the portion of the surgical environment by light having a single specified wavelength. In another example, spectrographic information could include the amplitude of light emitted from a portion of the surgical environment in response to illumination of the portion of the surgical environment by light having a plurality of different wavelengths (i.e., a reflectance and/or absorbance spectrum), or a plurality of different polarizations, intensities, or other properties.

In some embodiments, a system includes a laser (or similar source of substantially monochromatic light) configured to illuminate a portion of a surgical environment. The system further includes a spectrometer (or similar optical imaging equipment) configured to detect light emitted from the portion of the surgical environment in response to illumination such that spectrographic information (e.g., an emission spectrum) can be determined for the portion of the surgical environment. This determination could be performed by a controller of the system. Such a controller could be further configured to determine some information about the portion of the surgical environment based on the determined spectrographic information, e.g., to determine that the portion contains a portion of tissue of a particular type, that the portion contains a portion of a surgical instrument or other foreign body, that the portion contains a fluorescent or other type of marker chemical(s), or some other determination or classification based at least on the determined and/or detected spectrographic information.

In some embodiments, a system includes a tunable laser configured to illuminate a portion of a surgical environment with illumination having a controllable wavelength. The system further includes a light sensor (or similar optical imaging equipment) configured to detect light emitted from the portion of the surgical environment in response to illumination (e.g., a photodetector, photodiode, phototransistor, or other photosensitive element(s)). Thus, spectrographic information (e.g., a reflectance and/or absorbance spectrum) can be determined for the portion of the surgical environment by illuminating the portion of the surgical environment with light having a plurality of different respective wavelengths during a respectively plurality of periods of time and detecting the amplitude (or other property) of light responsively emitted (e.g., reflected, absorbed, scattered) from the portion of the surgical environment during the plurality of periods of time. This operation of the system could be performed by a controller of the system. Such a controller could be further configured to determine some information about the portion of the surgical environment based on the determined spectrographic information, e.g., to determine that the portion contains a portion of tissue of a particular type, that the portion contains a portion of a surgical instrument or other foreign body, that the portion contains a fluorescent or other type of marker chemical(s), or some other determination or classification based at least on the determined and/or detected spectrographic information.

Spectrographic information (and determinations or other processes performed based on such information) could be determined for a particular portion of a surgical environment or for a plurality of portions of the surgical environment. Determination of spectrographic information for an area of a surgical environment could be performed by illuminating and/or detecting light from a plurality of spots or other sub-regions of the area of the surgical field. For example, spots, lines, or other portions of the surgical environment could be illuminated by focusing a beam from a light source. Further, a light sensor could be configured to detect light from specified spots, lines, or other portions of the surgical environment. Additionally or alternatively, determination of spectrographic information for an area of a surgical environment could be performed by illuminating and/or detecting light from the entire area at once (e.g., by imaging the area using a CCD, an array of active pixel sensors, or some other imaging device).

Determined spectrographic information for a portion of a surgical environment could be used in a variety of ways to determine the identity of contents and/or one or more properties of the contents of the portion of the surgical environment. For example, a classifier could be used to determine that the portion of the surgical environment contains a portion of a surgical implement or other foreign body, that the portion of the surgical environment contains a portion of tissue of a particular type (e.g., connective tissue, blood vessels, blood, white matter brain tissue, grey matter brain tissue, cancerous tissue, muscle tissue), that the portion of the surgical environment contains a particular marker or contrast agent (e.g., a fluorophore, a chromophore, a Raman dye, a nanodiamond, a conductive nanostructure), or some other state or property of the portion of the surgical environment. Such classifiers could additionally be used to determine that the portion of the surgical environment contains a combination of tissues and/or objects.

Such classifiers could include a variety of algorithms and/or combinations of algorithms, including support vector machines, k-means clustering, neural nets, principal component or other dimensionality reductions, or other classification techniques or algorithms. Further, such classifiers could be created from supervised learning (e.g., trained using a number of samples having known contents or some other known property). Additionally or alternatively, such classifiers could be trained wholly or partially using unsupervised learning techniques.

Determined information about the identity or other properties of contents of a portion of a surgical environment could be used to enable a variety of applications. For example, such information could be used to determine the extent, location, or other information about tissues in a surgical field (e.g., the location and extent of an aggregation of cancerous cells in a tissue, of a nerve, of a blood vessel). Such information could be used to guide and/or plan a surgical intervention (e.g., to excite, ablate, debride, or otherwise remove a target tissue). For example, such information could be presented to a surgeon (e.g., on the display of a device and/or through an augmented reality head-mounted display) such that the surgeon could operate a scalpel, cautery tool, laser, RF, and/or contact thermal ablation tool, a surgical tele-robot, cryosurgical implement, a high-intensity focused ultrasound (HIFU) instrument, or some other surgical tool(s). Additionally or alternatively, a computer-guided surgical implement (e.g., a computer-controlled carbon-dioxide laser configured to ablate tissue through heating) could be operated according to such determined information (e.g., the computer-controlled laser could be operated to ablate tissues in regions of the surgical field determined, using spectrographic data, to contain cancer cells and not to contain surgical instruments or other foreign bodies). Other applications of and/or operations relative to determined spectrographic information are anticipated.

Other configurations, modes and methods of operation, and other embodiments are anticipated. System and/or methods described herein could include additional imaging modalities to improve the identification of the contents of portions of a surgical environment according to an application. A system as described herein could include multiple light emitters, multiple light sensors, and/or additional components according to an application. The system could be applied toward implementing, planning, and/or assessing a surgical intervention (e.g., ablation of a tissue), imaging a tissue, or some other application. Further, systems as described herein could be applied to the identification of the contents of portions of environments other than surgical environments (e.g., food processing environments, industrial fabrication environments, environments under study in scientific research) by determining spectrographic information about the portions of the other environments. Other applications and configurations of systems as described herein are anticipated.

It should be understood that the above embodiments, and other embodiments described herein, are provided for explanatory purposes, and are not intended to be limiting.

Further, the term "surgical intervention" as used herein should be understood broadly to include any activities applied toward the modification of the anatomy and/or tissue(s) of a human or animal body by the application of external forces and/or energies to the human or animal body; e.g., incision, ablation and/or cauterization by RF or other directed energies, excision, resection, suturing, application of surgical adhesives, stapling, transplanting, cauterizing, sawing, abrading, applying a surgical fluid to (e.g., sterile, isotonic saline), cooling, heating, or any other surgical operation or procedure.

II. Example Surgical Environment and Spectrographic Content

FIG. 1 illustrates an example surgical environment 100. The surgical environment 100 includes biological tissues (e.g., 130, 140, 150, 160, 170) that are subject to a surgical intervention using surgical instruments (e.g., 110, 120a, 120b) and other foreign bodies (e.g., 180). The biological tissues include skin 130 that has been cut a retracted away and muscles 140, 160 exposed by the retraction of the skin 130. The first muscle 140 has a tendon 150, and a blood vessel 170 is present on the surface of the muscles 140, 160. Further, a fluorophore (e.g., a fluorescent dye, a fluorescent marker configured to selectively interact with an analyte in the muscle 145) is present in a fluorescent portion 145 of the first muscle 140. The surgical instruments and other foreign bodies include a retractor having blades 120a, 120b being operated to retract the skin 130 to expose the underlying biological tissues (e.g., 140, 150, 160, 170, 145). A hemostat 110 that is clamping the blood vessel 170, and sutures 180 that have been sewn into the second muscle 160 (e.g., to close a wound or other cut or incision). The hemostat 110 has a fluorescent portion 115 (e.g., that is contaminated with a fluorophore, e.g., is coated with a fluorescent dye) that has similar fluorescent properties (e.g., emission wavelength(s), excitation wavelength(s)) as the fluorescent portion 145 of the first muscle 140. Note that the illustration of muscle tissue and other tissues, surgical instruments, and/or foreign bodies in FIG. 1 and elsewhere herein are intended as non-limiting illustrative examples. Systems and methods described herein could additionally or alternatively be applied to other organs, tissues, and tissue types, e.g., liver tissue, kidney tissue, connective tissue, pancreatic tissue, bowel tissue, prostate tissue, cortical tissue, nerve tissue, lung tissue, or some other type or types of tissue at some other location(s) of a body.

The biological tissues (e.g., 130, 140, 145, 150, 160, 170), surgical instruments (e.g., 110, 120a, 120b), and other foreign bodies (e.g., 180) in the surgical environment 100 could, respectively, have a number of properties relating to receiving, emitting, modifying, or otherwise interacting with electromagnetic energy (e.g., visible light, ultraviolet light, infrared light). A particular element (e.g., the hemostat 110) or portion of an element (e.g., the fluorescent portion 145 of the first muscle 140) in the surgical environment could have a wavelength-dependent interaction with electromagnetic radiation, i.e., the particular element could have an absorption, reflection, scattering, excitation, emission, or other type of spectrum related to the wavelength dependence of the absorption, reflection, scattering, emission, or other type of interaction between the particular element and electromagnetic radiation.

For example, an absorption or other spectrum of a biological tissue could be related to the presence of water, melanin, hemoglobin, or other substances in the tissue. In another example, an excitation and/or emission spectrum of a biological tissue, surgical instrument, or other foreign body could be related to the presence of one or more fluorophores or other fluorescent elements on or within in the biological tissue, surgical instrument (e.g., a contamination of fluorescent dye on the surface of the surgical instrument), or other foreign body. In some examples, an absorbance and/or reflectance spectrum of a metallic surgical instrument or foreign body, or a metallic portion thereof, could be related to a composition, geometry, surface texture, electron band structure, or other property of the metallic surgical instrument, foreign body, or portion thereof. Properties of a biological tissue (e.g., absorption spectrum, excitation spectrum, emission spectrum) could be related to a medical state of the biological tissue. For example, a cancerous tissue could have an absorbance spectrum (e.g., could be a different color) different from the absorbance spectrum of a non-cancerous tissue. Additionally or alternatively, a fluorophore, chromophore, or other marking agent could be introduced (e.g., by direct application, by injection into the bloodstream of a person) to a particular tissue (e.g., a cancerous tissue) and one or more spectrographic properties of the marking agent and/or of the combination of the marking agent and the particular tissue could be detected to determine the location, shape, or other properties of the particular tissue. Such a marking agent could be configured to selectively interact with a particular tissue (e.g., by binding to a protein or other element specific to the particular tissue) such that systemic application of the marking agent (e.g., by injection into the bloodstream of a person) could allow the marking agent to be concentrated in the particular tissue. In another example, the absorption spectrum of a tissue could be related to the amount of oxygenation of hemoglobin in the tissue, such that the oxygen content, perfusion rate, or other information about the tissue could be determined based on a determined and/or detected absorption spectrum or features thereof.

Spectrographic information about a biological tissue, surgical instrument, foreign body, or other portion of a surgical environment could be detected and/or determined by illuminating the portion of the surgical environment, detecting light that is emitted from the portion in response to the illumination, and determining some spectrographic content of the received light. Determining spectrographic content could include generating a spectrum (e.g., a reflectance spectrum, an emission spectrum, an absorbance spectrum) from the received light by detecting the a plurality of amplitudes of the received light within a respective plurality of ranges of wavelengths. That is, the spectrographic content could include a plurality of detected and/or determined amplitudes corresponding to wavelengths of the received light, e.g., at specified wavelengths linearly spaced within a range of wavelengths. Such a determined spectrographic content could be generated related to the illumination of the contents by light of a single wavelength. Alternatively, such spectrographic content could be determined a plurality of times corresponding to illumination of the contents during a respective plurality of different periods of time by light of a respective plurality of different single wavelengths.

Spectrographic contents could include a description of one or more features of a spectrum or other wavelength-dependent optical properties of the contents; for example, spectrographic content could include an absolute or relative amplitude, mean wavelength, width at half maximum, or other descriptive information about a peak or other feature of a spectrum of a portion of a surgical environment. Such spectrographic contents could be determined based on a determined and/or detected spectrum (e.g., by extracting an amplitude, width, or wavelength location of a peak within a determined and/or detected plurality of detected amplitudes corresponding to wavelengths of light received from the surgical environment). Alternatively, such spectrographic contents could be determined in other ways, e.g., through an iterative process that includes controlling a wavelength of light illuminating a portion of the surgical environment to minimize an amplitude of light received from the portion in response to the illumination, e.g., to determine a wavelength of a peak within the absorbance spectrum of the portion. Other types of spectrographic contents and methods of detecting and/or determining such spectrographic contents are anticipated.

In some examples, one or more spectra of a biological tissue, surgical instrument, foreign body, or other object in the surgical environment could be altered by the addition of a fluorophore, chromophore, pigment, dye, coating, or other substance according to an application. For example, a fluorophore configured to selectively interact with an analyte (e.g., with an enzyme, protein, marker, or other element expressed by cancer cells) could be introduced into a body containing tissues subject to a surgical intervention (e.g., a body of a person to be surgically treated for cancer) such that the analyte could be detected, localized, and/or identified in the tissue using methods as described herein. Such identification could be performed to guide the ablation, resection, removal, or other surgical modification or interaction with a tissue containing the analyte. This could include presenting imaging information related to the identification of the analyte throughout an imaged surgical environment, operating a surgical laser or other automated or semi-automated surgical instrument relative to the identified tissues containing the analyte, or according to some other method. Additionally or alternatively, an introduced fluorophore, chromophore, pigment, dye, coating, or other substance could have one or more spectrographic properties (e.g., an amplitude, center wavelength, width, or other property of a peak within an absorption or other spectrum of the introduced substance) that are related to properties (e.g., a temperature, a pH, an osmolality, a strain, a stress, a pressure) of one or more portions of a surgical environment. In some examples, such an introduced substance could be introduced to mark the location of one or more biological tissues (e.g., to mark the location of a tumor detected using CT, MRI, palpation by a surgeon, or some other method).

Figure 2A:
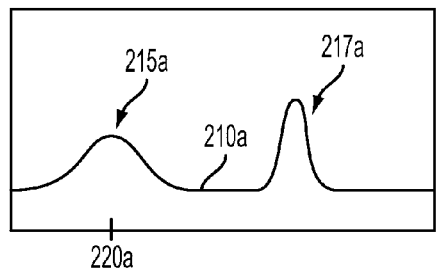
FIG. 2A illustrates example spectrographic content of light received from a portion of a surgical environment.

FIG. 2A illustrates a first example spectrum 210a of light received from a first portion of a surgical environment in response to illumination of the first portion by light having a specified wavelength. The horizontal axis indicates wavelength (increasing to the right) and the vertical axis indicates amplitude. The first example spectrum 210a illustrates the amplitude of light received from the first portion of tissue as a function of wavelength. Further, the wavelength of the illumination is illustrated by the first tick 220a. The first example spectrum 210a includes a first peak 215a having a center wavelength substantially equal to the wavelength of the illumination (220a) and a second peak 217a that is at a greater wavelength. The first peak 215a could correspond to illumination received by the first portion that is scattered, refracted, diffracted, reflected, or otherwise directed back toward a light sensor configured to detect light from the first portion. The second peak 217a could correspond to light emitted by fluorophores (e.g., elements of the first portion that can receive illumination at the wavelength of the illumination 220a and responsively emit light at a different, greater wavelength) of the first portion of the surgical environment in response to the illumination.

Figure 2B:
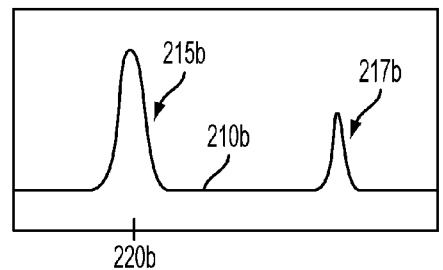
FIG. 2B illustrates example spectrographic content of light received from a portion of a surgical environment.

FIG. 2B illustrates a second example spectrum 210b of light received from a second portion of the surgical environment in response to illumination of the second portion by light having a specified wavelength equal to the specified wavelength of the light used to illuminate the first portion to generate the first example spectrum 210a. The horizontal axis indicates wavelength (increasing to the right) and the vertical axis indicates amplitude. The second example spectrum 210b illustrates the amplitude of light received from the second portion of tissue as a function of wavelength. Further, the wavelength of the illumination is illustrated by the first tick 220b. The second example spectrum 210b includes a first peak 215b having a center wavelength substantially equal to the wavelength of the illumination (220b) and a second peak 217b that is at a greater wavelength. The first peak 215b could correspond to illumination received by the second portion that is scattered, refracted, diffracted, reflected, or otherwise directed back toward a light sensor configured to detect light from the second portion. The second peak 217b could correspond to light emitted by fluorophores (e.g., elements of the second portion that can receive illumination at the wavelength of the illumination 220b and responsively emit light at a different, greater wavelength) of the second portion of the surgical environment in response to the illumination.

The first 210a and second 210b example spectra could be emission spectra of respective first and second portions of a surgical environment. A difference between the first and second portions of the surgical environment and/or an identity of the first and/or second portions could be determined based on features of the first 210a and second 210b example spectra. For example, a difference in the amount of a fluorophore could be determined based on a difference in amplitude of the second peak 217a, 217b between the first 210a and second 210b spectra. A tissue type of tissue in the first or second portions could be determined based on features or other information about the spectra. A tissue type could include one or more classifications applied to a portion of biological tissue (e.g., "muscle," "skeletal muscle," "pennate muscle," "fast-fatigue muscle," "tendon," "epithelium," "cartilage," "bone," "cortical bone," "blood," "vasculature," "artery," "vein," "lymph," "nerve," "fat," "smooth muscle," "necrotic tissue," "ischemic tissue," "neoplastic tissue," "cancerous tissue," "melanoma," "cyst" or some other class or classes of biological tissue). Further, the presence of a surgical instrument, suture, or other foreign body in the first or second portions could be determined. For example, the amplitude or other information about the first peak 217b in the second example spectrum 210b could indicate a high reflectivity or other optical property indicative of a metallic foreign body or surgical instrument. In a particular example, the first example spectrum 210a could correspond to a first portion of the surgical environment containing a portion of biological tissue that includes a fluorophore, and the second example spectrum 210b could correspond to a second portion of the surgical environment containing a portion of a metallic surgical instrument that is coated in an amount of a fluorophore dye. Other distinctions and/or identifications of portions of a surgical environment, based on additional or alternative features of a spectrum of the portions, are anticipated.

Contents of the first 210a and second 210b example spectra could be determined based on light received from the first and second portions using the same detector in response to illumination of the first and second portions by the same light source. For example, the first and second portions could be illuminated by a laser configured to control a direction of illumination emitted by the light source (e.g., by including galvanometers or other actuators configured to actuate mirrors or other optical elements of the light source) to illuminate different portions of the surgical environment. Further, amplitudes of light within specified wavelength ranges or other properties of light emitted by the first and second portions could be detected by a spectrometer configured to receive light from different portions of the surgical environment. Spectrographic contents determined from light received in such a way could include a set of the detected amplitudes, a description (e.g., amplitude, width, mean wavelength) of peaks or other features of the spectrum, or some other information.

Figure 2C:
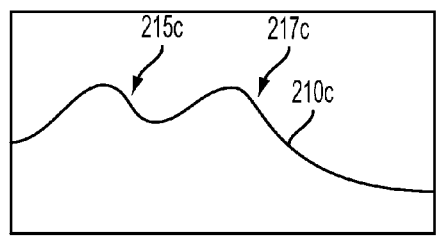
FIG. 2C illustrates example spectrographic content of light received from a portion of a surgical environment.

FIG. 2C illustrates a third example spectrum 210c of light received from a third portion of a surgical environment in response to illumination of the third portion by a plurality of lights having a variety of wavelengths. The horizontal axis indicates wavelength (increasing to the right) and the vertical axis indicates amplitude. The third example spectrum 210c illustrates the amplitude of light received from the third portion of tissue as a function of the wavelength of light illuminating the third portion of tissue. The third example spectrum 210c includes a first peak 215c and a second peak 217c. The first 215c and second 215c peaks could correspond to ranges of light that are less scattered, absorbed, or otherwise not directed back toward a light sensor configured to detect light from the third portion.

Figure 2D:
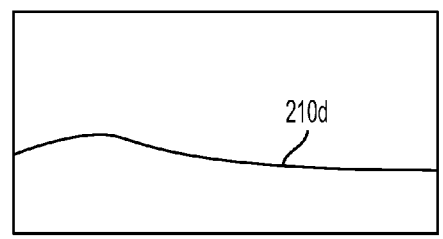
FIG. 2D illustrates example spectrographic content of light received from a portion of a surgical environment.

FIG. 2D illustrates a fourth example spectrum 210d of light received from a fourth portion of a surgical environment in response to illumination of the fourth portion by a plurality of lights having a variety of wavelengths. The horizontal axis indicates wavelength (increasing to the right) and the vertical axis indicates amplitude. The fourth example spectrum 210d illustrates the amplitude of light received from the fourth portion of tissue as a function of the wavelength of light illuminating the fourth portion of tissue.

Figure 2E:
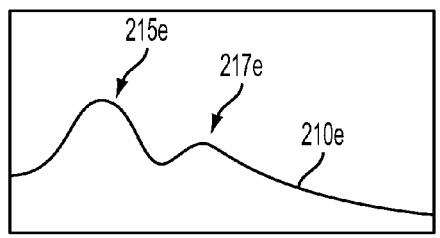
FIG. 2E illustrates example spectrographic content of light received from a portion of a surgical environment.

FIG. 2E illustrates a fifth example spectrum 210e of light received from a fifth portion of a surgical environment in response to illumination of the fifth portion by a plurality of lights having a variety of wavelengths. The horizontal axis indicates wavelength (increasing to the right) and the vertical axis indicates amplitude. The fifth example spectrum 210e illustrates the amplitude of light received from the fifth portion of tissue as a function of the wavelength of light illuminating the fifth portion of tissue. The fifth example spectrum 210e includes a first peak 215e and a second peak 217e. The first 215e and second 215e peaks could correspond to ranges of light that are less scattered, absorbed, or otherwise not directed back toward a light sensor configured to detect light from the fifth portion.

The third 210c, fourth 210d, and fifth 210e example spectra could be absorption spectra of respective third, fourth, and fifth portions of a surgical environment. A difference between the third, fourth, and/or fifth portions of the surgical environment and/or an identity of the third, fourth, and/or fifth portions could be determined based on features of the third 210c, fourth 210d, and fifth 210e example spectra. For example, the third and fifth portions of the surgical environment could be portions of biological tissue containing a chromophore (e.g., hemoglobin) having one or more optical properties related to a state of the chromophore and/or of a biological tissue containing the chromophore (e.g., an absorbance at one or more wavelengths related to an oxygenation state of the tissue and/or of the chromophore). Thus, a relative state (e.g., a relative level of oxygenation) of the third and fifth portions could be determined based on a difference between the third 210c and fifth 210e example spectra (e.g., a relative amplitude of the first 215c, 215e and/or second 217c, 217e peaks). A tissue type of tissue in the third, fourth, and/or fifth portions could be determined based on features or other information about the spectra. Further, the presence of a surgical instrument, suture, or other foreign body in the third, fourth, and/or fifth portions could be determined. For example, a shape, smoothness, or other information about the fourth example spectrum 210d through a range characterized by less smooth spectra in biological tissue could indicate that the fourth portion of the surgical environment contains a portion of a metallic foreign body or surgical instrument. Other distinctions and/or identifications of portions of a surgical environment, based on additional or alternative features of spectra of the portions, are anticipated.

Contents of the third 210c, fourth 210d, and fifth 210e example spectra could be determined based on light received from the third, fourth, and fifth portions using the same detector in response to illumination of the third, fourth, and fifth portions by the same light source. For example, the third, fourth, and fifth portions could be illuminated by a tunable laser (e.g., a laser configured to emit a beam having a controllable wavelength and/or a set of lasers configured to emit beams having different wavelengths) configured illumination an area of the surgical environment containing the third, fourth, and fifth portions (e.g., by including a beam spreader or other optical element(s) to widen a beam emitted by the tunable laser). Further, amplitudes or other properties of light emitted by the third, fourth, and fifth portions could be detected by a camera or other photodetector configured to receive light from different portions of the surgical environment. Spectrographic contents determined from light received in such a way could include a set of amplitudes of light detected from one or more portions of the surgical environment (e.g., detected using more or more pixels of a camera) corresponding to a set of lights (having respective different wavelengths) used to illuminate the one or more portions, a description (e.g., amplitude, width, mean wavelength) of peaks or other features of the spectrum, or some other information.

Note that the example spectra (e.g., 210a, 210b, 210c, 210d, 210e) and their relationships to properties of corresponding example portions of a surgical environment are meant to illustrate by example and are not intended to be limiting. Other methods of detecting and/or determining spectrographic information and/or content for one or more portions of a surgical environment are anticipated. Further, additional or alternative methods of identifying the contents and/or properties of a portion of a surgical environment based on determined spectrographic content corresponding to the portion are anticipated.

Such spectrographic content and/or information determined therefrom (e.g., determination that spectrographic content corresponds to a biological tissue, to a particular type of biological tissue, to a surgical instrument or other foreign body) could be determined for a plurality of portions of a surgical environment. This could be performed sequentially for a series of portions of the surgical environment (e.g., by scanning a laser configured to emit a beam of illumination to illuminate a spot, line, or other-shaped region containing portions of the surgical environment, by scanning a direction of focus and/or sensitivity of a light detector across a plurality of portions of the surgical environment). Additionally or alternatively, a camera or other sensor containing a plurality of light-sensitive components could be operated to receive light from a plurality of corresponding portions of the surgical environment in response to illumination of the plurality of portions of the surgical environment. Such information about a plurality of portions of a surgical environment could be used to determine spectrographic or other images of the surgical environment.

Figure 3A:
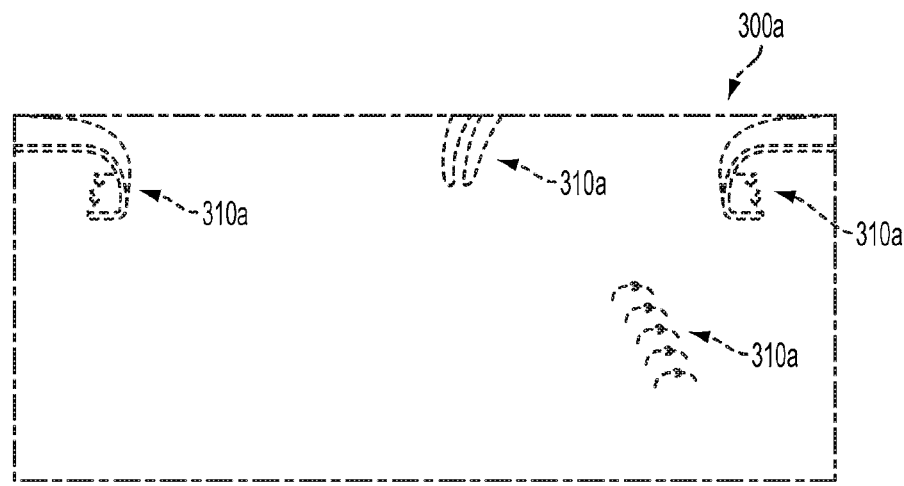
FIG. 3A illustrates an example image of the surgical environment of FIG. 1 determined based on spectrographic content of light received from the surgical environment.

As an illustrative example, FIG. 3A illustrates a first example image 300a of the surgical environment 100. The first example image 300a indicates portions 310a of the surgical environment 100 that contain surgical instruments, sutures, or other foreign bodies. The first example image 300a is determined based on determined spectrographic contents corresponding to a plurality of portions of the surgical environment 100 spanning the field of view of a surgical imaging system or other apparatus configured to illuminate portions of the surgical environment, to receive light from the illuminated portions, and to determine the spectrographic content of the received light. Such an image could be presented to a surgeon or other user to inform some action of the user (e.g., to determine that all sutures, drains, pads, catheters, sponges, gauze, staples, other medical supplies, and/or other foreign bodies have been removed from the surgical environment). Such an image could additionally or alternatively be used to inform the operation of an automated surgical instrument, e.g., to specify regions of the surgical environment that should not be exposed to the output of a surgical laser.

Figure 3B:
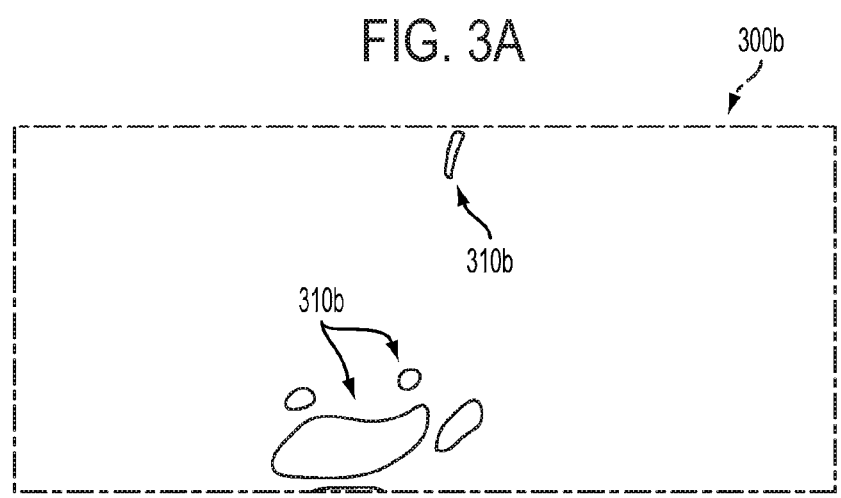
FIG. 3B illustrates an example image of the surgical environment of FIG. 1 determined based on spectrographic content of light received from the surgical environment.

FIG. 3B illustrates a second example image 300b of the surgical environment 100. The second example image 300b indicates portions 310b of the surgical environment 100 that contain a fluorophore. The second example image 300b is determined based on determined spectrographic contents corresponding to a plurality of portions of the surgical environment 100 spanning the field of view of a surgical imaging system or other apparatus configured to illuminate portions of the surgical environment, to receive light from the illuminated portions, and to determine the spectrographic content of the received light. Such an image could be presented to a surgeon or other user to inform some action of the user (e.g., to determine the location and extent of a labeled tissue or surgical instrument, to determine the degree of ablation of such a tissue in response to the operation of a surgical laser). Such an image could additionally or alternatively be used to inform the operation of an automated surgical instrument, e.g., to specify regions of the surgical environment that should be ablated by application of the output of a surgical laser.

Figure 3C:
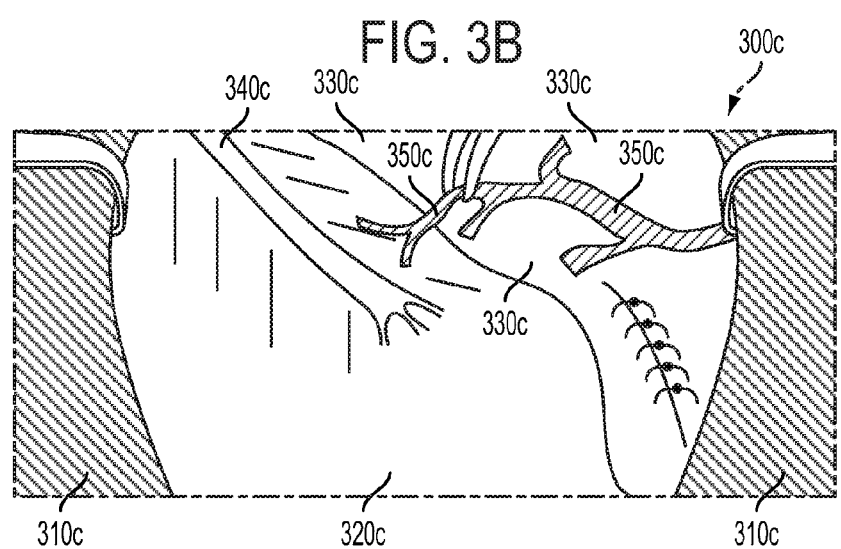
FIG. 3C illustrates an example image of the surgical environment of FIG. 1 determined based on spectrographic content of light received from the surgical environment.

FIG. 3C illustrates a third example image 300c of the surgical environment 100. The third example image 300c indicates the type of tissue contained by portions of the surgical environment 100. Tissue types include skin 310c, a first muscle tissue 320c, tendon 340c, a second muscle tissue 330c, and blood vessel tissue 350c The third example image 300c is determined based on determined spectrographic contents corresponding to a plurality of portions of the surgical environment 100 spanning the field of view of a surgical imaging system or other apparatus configured to illuminate portions of the surgical environment, to receive light from the illuminated portions, and to determine the spectrographic content of the received light. Such an image could be presented to a surgeon or other user to inform some action of the user (e.g., to determine the location and extent of a diseased tissue, to determine a health or other state of such a tissue). Such an image could additionally or alternatively be used to inform the operation of an automated surgical instrument, e.g., to specify regions of the surgical environment that should or should not be ablated by exposure to the output of a surgical laser.

Such images of a surgical environment (e.g., 300a, 300b, 300c) and/or information about a portion of a surgical environment could be determined based on determined spectrographic contents of light received from the surgical environment and/or portion thereof in a variety of ways. Generally, spectrographic contents for a particular portion of a surgical environment could be used by a processor, controller, or other computational system to identify a portion of tissue, a portion of a surgical instrument, a portion of a foreign body, or some other contents of the portion of the surgical environment. This could include the controller applying a classifier to the determined spectrographic contents to generate an identifier (e.g., 'surgical instrument,' 'retractor,' 'foreign body,' 'biological tissue,' 'tumor,' 'blood vessel,' 'nerve,' 'muscle') or other information for the portion of the surgical environment. The spectrographic contents could include vectors of amplitude or other detected properties of the received light (e.g., vectors of amplitudes corresponding to received light within corresponding ranges of wavelengths), information (e.g., amplitudes, center wavelengths, peak widths, fall-off rates) about features (e.g., peaks, troughs, slopes, inflections) of a spectrum of received light, or some other information about received light. In some examples, spectrographic information corresponding to light received from a surgical instrument contaminated with a fluorophore or other marking agent could be intermediate between spectrographic information corresponding to the marking agent alone and spectrographic information corresponding to an uncontaminated surgical instrument.

A controller could implement a variety of classifiers and/or combinations of classifiers to identify or otherwise assign a classification to a portion of a surgical environment based on a spectrographic contents of light received from the portion. Classifiers could generate a binary output (e.g., "biological tissue" vs. "not biological tissue") or an output having a plurality of possible states (e.g., "artery," "vein," "nerve," "tendon," "skin," "muscle," "fat," "necrosis," "tumor"). A plurality of possible outputs states could be nominal (i.e., categorical and non-ordered) or ordinal (e.g., "very unlikely to contain cancer cells," "slightly unlikely to contain cancer cells," "slightly likely to contain cancer cells," "very likely to contain cancer cells"). Output of a classifier corresponding to a particular portion of a surgical environment could be based only on spectrographic content from the particular portion or could be based additionally on spectrographic content from other portions of the surgical environment (e.g., neighboring portions of the surgical environment to enable a spatially smooth output of the classifier across portions; a portion of the surgical environment containing a calibration object having known spectrographic properties to act as a baseline for comparison). A classifier could generate multiple outputs for a single portion (e.g., could output one of "biological tissue" and "surgical instrument" and one of "contains fluorophore" and "does not contain fluorophore"). Such multiple outputs of a classifier could be used to make a further determination about the single portion, e.g., that the single portion contains a surgical instrument or other foreign body contaminated with a fluorophore.

Classifiers implemented by a controller could include linear classifiers, nonlinear classifiers, support vector machines, decision trees, k-nearest-neighbors, neural networks, thresholds, or other classifiers and/or combinations thereof. Further, a controller could perform some preprocessing on input spectrographic content before the application of a classifier. For example, input content could be subject to some transformation (e.g., conversion by application to a logarithmic, hyperbolic, power series, or other nonlinear function), dimensionality reduction (e.g., principal components analysis, factor analysis, independent components analysis, isomap, linear discriminant analysis, non-negative matrix factorization), filtering (e.g., spatial filtering across spectrographic contents for neighboring portions, wavelength filtering to smooth a determined spectrum) or some other preprocessing step.

Parameters, structures, weights, or other properties of such classifiers could be determined in a variety of ways. In some examples, classifiers could be specified by supervised learning, wherein determined spectrographic contents for a set of known portions of a surgical environment (e.g., a set of portions whose identity is determined by a human being) along with the known classifier outputs corresponding to such spectrographic contents are used to train a classifier (e.g., to set weights, parameters, or the overall structure of a classifier). This could include performing a scan of a surgical environment containing a variety of contents (e.g., containing both biological tissues and non-biological elements, containing a variety of different types of biological tissues) and receiving a set of classifications corresponding to portions of the surgical environment (e.g., by receiving such classifier information from a surgeon). This could include performing a scan to determine spectrographic contents of light received from isolated biological tissues, surgical instruments, or other objects and receiving a set of classifications corresponding to the isolated objects. In some examples, spectrographic contents corresponding to a variety of biological tissues, surgical instruments, or other objects could be determined in simulation (e.g., by simulating the interaction of light with a model of a biological tissue or other object).

Additionally or alternatively, parameters, structures, weights, or other properties of such classifiers could be determined by unsupervised learning. For example, a controller could determine spectrographic contents for a plurality of portions of a surgical environment and could then specify a classifier to categorize the portions using an unsupervised learning algorithm. Determined regions of the surgical environment having similar classifications could then be identified by a surgeon or could be used according to some other application.

Information about a portion of a surgical environment (e.g., the identification of a portion of the surgical environment as containing a portion of biological tissue, the determination of a tissue type of or other information about such a portion of biological tissue, the identification of a portion of the surgical environment as containing a portion of a surgical instrument, suture, or other foreign body) could be determined based on determined spectrographic contents of light received from the portion in response to illumination of the portion could be used for a variety of applications. For example, such determined information could be displayed to a surgeon, pathologist, or other person to inform some course of action; e.g., to inform a surgical intervention (e.g., to indicate the location and extent of a diseased tissue to be incised, resected, ablated, or otherwise modified), to inform a course of treatment. Additionally or alternatively, such information could be used to implement a surgical intervention by a robotic surgical system.

Automated surgical interventions (e.g., surgical interventions performed wholly or partially by the operation of an artificial system) could include implementing some interaction with a target tissue (e.g., ablating a tissue containing cancer cells) while avoiding interaction with other biological tissues and/or non-biological contents of a surgical environment. In some examples, a surgical environment could contain a variety of surgical instruments (e.g., retractors, hemostats) and other foreign bodies (e.g., fiducials, screws, staples, sutures). For example, operation of an automated surgical laser configured to ablate tissue could include avoiding application of the output of the surgical laser to such surgical instruments or other foreign bodies. Application of the output to such contents of the surgical environment could cause unwanted effects, including but not limited to destruction of the surgical instruments or other foreign bodies (e.g., the destruction of a suture allowing tissues secured, ligated, or otherwise influenced by the suture to become loose), release of toxic or otherwise counter-indicated chemicals from heating and/or ablation of the surgical instruments or other foreign bodies, and uncontrolled optical effects on the light emitted by the surgical laser (e.g., reflection of a laser beam toward other portions of the surgical environment, potentially damaging biological tissues of a patient receiving the surgical intervention and/or nearby medical personnel). In some examples, the surgical environment could include blood vessels, nerves, tendons, or other sensitive tissues and performance of a surgical intervention (e.g., ablation) on such tissues could cause a negative outcome (e.g., blood loss, tissue necrosis, muscle paralysis, loss of sensation).

Information about the identity of portions of a surgical environment determined using spectrographic methods as described herein could be used to inform the performance of such wholly or partially automated surgical interventions. In some examples, this could include determining regions of the surgical environment to avoid interaction with. For example, a portion of the surgical environment could be determined to contain among other things (e.g., a portion of biological tissue) a portion of a surgical instrument, suture, or other foreign body, and this determination could be used by an automated surgical system to avoid ablating, heating, or otherwise directing energy toward or interacting with the portion of the surgical environment. In another example, a portion of the surgical environment could be determined to contain a portion of biological tissue of a certain type (e.g., a nerve, a blood vessel, a tissue that does not contain cancer cells), and this determination could be used by an automated surgical system to avoid ablating, heating, or otherwise directing energy toward or interacting with the portion of the surgical environment. In some examples, such information about the identity of portions of a surgical environment could be used to determine the efficacy and/or effects of an automated or other surgical intervention, e.g., to determine whether a cancerous tissue has been fully ablated by the operation of a surgical laser or other surgical instrument.

Figure 4A:
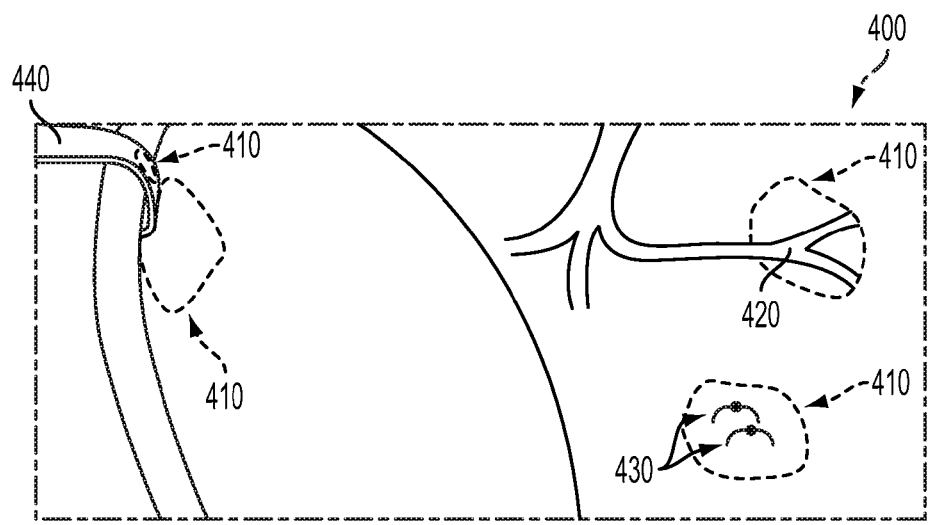
FIG. 4A illustrates an example surgical environment containing a fluorophore.

To illustrate the use of methods as described herein to inform automated and/or manual surgical interventions, FIG. 4A illustrates an example surgical environment 400. The surgical environment 400 includes biological tissues (e.g., skin, muscle, a blood vessel 420) that are subject to a surgical intervention using surgical instruments (e.g., a retractor 440) and other foreign bodies (e.g., sutures 430). Further, a fluorophore configured to selectively interact with an analyte in the biological tissue is present in fluorescent portions 410 of the surgical environment in the biological tissue and on the surface of the retractor 440. An automated surgical laser could be configured to emit a beam to ablate biological tissue and could be operably coupled to a surgical imaging system configured to illuminate portions of the surgical environment 400 and to receive light emitted by the portions of the surgical environment 400 in response to the illumination. Operation of a controller of the surgical imaging system to generate the example image 405 from determined spectroscopic contents corresponding to portions of the surgical environment 400 could include implementing a single classifier and/or multiple classifiers combined together. For example, the controller could determine a first output of a first classifier specified to determine that a portion of the surgical environment contains the fluorophore and a second output of a second classifier specified to determine whether a portion of the surgical environment contains a portion of biological tissue that is not a blood vessel. The example image 405 could be determined by the controller by combining the first and second outputs to generate an overall output of the combined classifier that comprises the first and second classifiers.

Figure 4B:
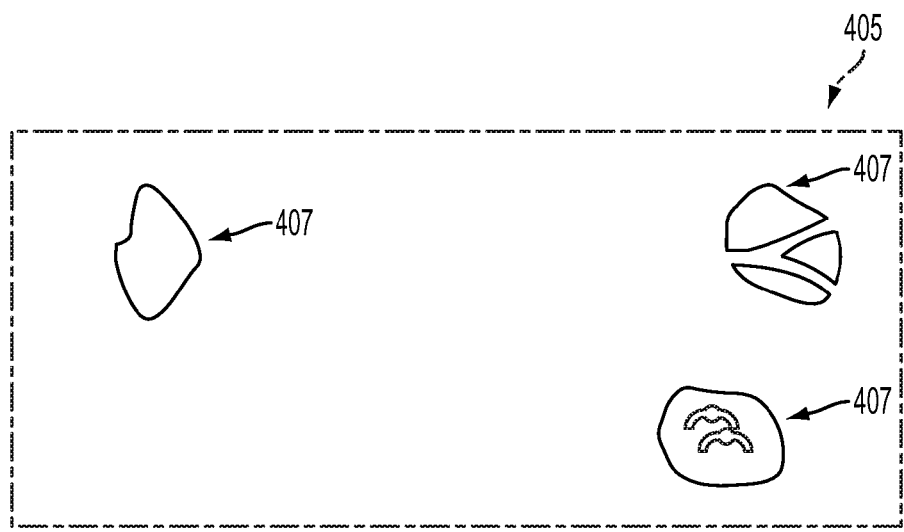
FIG. 4B illustrates an example image of the surgical environment of FIG. 4A determined based on spectrographic content of light received from the surgical environment.

A controller of the surgical imaging system could be configured to operate elements of the surgical imaging system (e.g., light sources, light detectors) to determine spectrographic content of light received from portions of the surgical environment and to identify portions of the surgical environment based on the determined spectrographic content. This could include determining portions of the surgical environment that contain biological tissue that contains the analyte by determining portions of the surgical environment that contain biological tissue and that contain the fluorophore. For example, FIG. 4B illustrates an example image 405 of the surgical environment 400. The example image 405 indicates portions 407 of the surgical environment 400 that contain biological tissue marked by the fluorophore and that do not contain elements that should not be exposed to energy emitted by the surgical laser (e.g., the blood vessel 420, the retractor 440, the sutures 430).

The example image 405 is determined based on determined spectrographic contents corresponding to a plurality of portions of the surgical environment 400 spanning the field of view of the surgical imaging system. Such an image could be presented to a surgeon or other user to inform some action of the user. For example, such an image could be presented to guide the surgeon in operating a surgical laser or other surgical instrument to ablate tissue containing the fluorophore without damaging or otherwise interacting with structures that could be damaged by the laser or whose exposure to the surgical laser could otherwise have a negative effect (e.g., the blood vessel 420, the retractor 440, the sutures 430). Such an image could additionally or alternatively be used by the controller to operate the surgical laser, e.g., to ablate regions of the surgical environment containing the fluorophore but without damaging or otherwise interacting with the blood vessel 420, sutures 430, and retractor 440.

The identifying a portion of the surgical environment as containing a portion of a biological tissue, a portion of a particular type of biological tissue, a portion of a surgical instrument, or some other identification could be based on information other than determined spectrographic content of light received from the portion of the surgical environment. For example, information from other imaging modalities or systems could be combined with determined spectrographic content to identify to portion of the surgical environment. For example, a CT scanner, ultrasound scanner, MR imager, or other device or combination of devices could be used to determine information about the portion of the surgical environment and the determined information could be used alone or in combination with the determined spectrographic content to identify the portion of the surgical environment.

III. Example Surgical Spectrographic Imaging Systems

Generally, a surgical imaging system as described herein include at least one light source configured to illuminate one or more portions of a surgical environment with light having one or more specified properties and a detector configured to detect a spectrographic content of light received from the one or more illuminated portions of the surgical environment. The light source could be configured and/or operated to illuminate a plurality of portions simultaneously (e.g., by illuminating a large area of the surgical environment) or one portion at a time (e.g., by emitting a beam to illuminate a single portion (i.e., a spot), a line, or some other shape) and scanning across the surgical environment to illuminate a plurality of portions over time. The light source could emit light at a single wavelength (or light having some other properties that are substantially the same over time) or could emit light at a plurality of wavelengths during a plurality of different periods of time. The detector could detect light within a single narrow range of wavelengths, within a wide range of wavelengths, and/or within a plurality of ranges of wavelengths. Further, the detector could be configured to receive light from a particular portion of the surgical environment (e.g., could include optics to focus the detector on a particular portion), a wide area of the surgical environment, or a plurality of portions of the surgical environment simultaneously (e.g., the detector could include a camera or other device including a plurality of light sensors configured to receive light from a respective plurality of portions of the surgical environment). A variety of combinations and configurations of light sources and detectors are anticipated.

The one or more light sources, detectors, controllers configured to operate such, and/or other components of a surgical imaging system as described herein could be disposed in a single housing or other apparatus or could be separate and put in communication with each other by one or more means known to one of skill in the art (e.g., cabling, wireless communication). Such a system could be handheld, attached to an armature, or maintained at a location proximate to a target surgical environment by some other means. A controller configured to determine spectrographic content of light received by a detector of the surgical imaging system, to identify a portion of the surgical environment based on such content, and/or perform some other operations could be located proximate to the light source and/or detector (e.g., could be disposed in a housing that also contains the light source and/or detector) or could be remote from those elements and could be in communication with those elements (e.g., via cabling, a wireless link, the internet, or some other network).

Figure 5A:
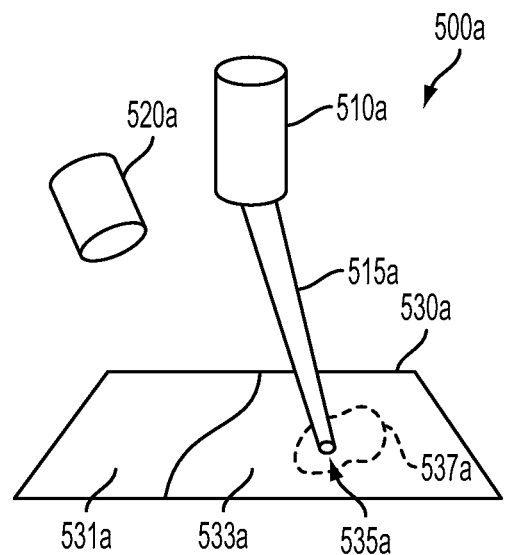
FIG. 5A illustrates an example system imaging a surgical environment.

FIG. 5A illustrates elements of a first example surgical imaging system 500a including a light source 510a and a detector 520a. The light source 510a is configured to emit a beam of illumination 515a containing light at a specified wavelength and to illuminate a spot on the biological tissue 530a. The biological tissue includes a first muscle 531a and a second muscle 533a. The detector 520a is configured to receive light from an area of the biological tissue 530a and to generate information about the spectrographic contents of the received light. The second muscle 533a includes a tagged region 537a containing a fluorophore configured to selectively interact with an analyte that is present in the tagged region 537a. Further, the tagged region 537a includes a portion of tissue 535a that is being illuminated by the light source 510a during a period of time illustrated in FIG. 5A The light source 510a could include a variety of light-emitting elements configured to produce light at substantially one wavelength (i.e., containing light of wavelengths within a specified narrow range of wavelengths). This could include lasers, light-emitting diodes (LEDs), or other substantially monochromatic light sources. Additionally or alternatively, the light source 510a could include a light emitting element that emits light across a wider range of wavelengths, and this non-monochromatic light could be emitted through one or more filters (e.g., filters including one or more Bragg reflectors, prisms, diffraction gratings, slit apertures, monochromators) configured to only allow the transmission of light within a narrow range of wavelengths. The light source 510a could include mirrors, lenses, diffraction gratings, or other optics controlled by galvanometers, motors, or other actuators to control the direction of the beam of illumination 515a such that the location of a portion of the surgical environment 530a could be controlled (e.g., by a controller operably coupled to the light source 510a).

The detector 520a could include one or more light-sensitive elements configured to detect the amplitude or other properties of light received by the detector 520a within one or more respective ranges of wavelengths. That is, the detector 520a could be configured to act as a spectrometer, receiving light from the biological tissue 530a and outputting information related to the spectrum of the received light (i.e., outputting information relating to the spectrographic content of the received light). This could include the detector 520a containing a prism and a linear (or otherwise arranged) array of light sensitive elements (e.g., photodiodes, phototransistors, pixels of a charge-coupled device (CCD), active pixel sensors) configured such that the output of an individual light sensitive element is related to the amplitude of the received light within a specified range of wavelengths. Other configurations of the detector 520a to enable the detection and/or determination of the spectrographic content of light received by the detector 520a are anticipated. The detector 520a is configured to receive light from a plurality of portions of the biological tissue 530a within an area of view of the surgical imaging system 500a.

Figure 5B:
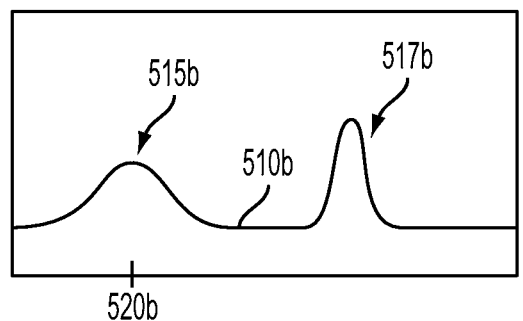
FIG. 5B illustrates example spectrographic content of light received from a portion of the surgical environment of FIG. 5A by the system of FIG. 5A.

Spectrographic content of light received by the surgical imaging system 500a from a portion of a surgical environment (e.g., from the portion of tissue 535a) could take the form of an emission or other spectrum of the received light (e.g., a vector or other arrangement of detected amplitudes of the received light within corresponding specified ranges of wavelengths). An example of such spectrographic content is illustrated in FIG. 5B. FIG. 5B includes an example spectrum 510b of light received from the portion of tissue 535a in response to illumination of the portion of tissue 535a by the beam of illumination 515a. The horizontal axis indicates wavelength (increasing to the right) and the vertical axis indicates amplitude. The example spectrum 520b illustrates the amplitude of light received from the portion of tissue 535a as a function of wavelength. Further, the wavelength of the beam of illumination 515a is illustrated by the first tick 520b. The example spectrum 510b includes a first peak 515b having a center wavelength substantially equal to the wavelength of the beam of illumination 515a and a second peak 517b that is at a greater wavelength. The first peak 515b could correspond to illumination received by the portion of tissue 535a that is scattered, refracted, diffracted, reflected, or otherwise directed back toward detector 520a. The second peak 517b could correspond to light emitted by the fluorophore in the portion of tissue 535a in response to being illuminated by the beam of illumination 515a.

To improve the signal-to-noise ratio, or according to some other application, the surgical imaging system 500a (or other example surgical imaging systems described herein, e.g., 600a, 700a, 800a, 900a) could be operated in a dim environment, could be configured to detect light within a range of wavelengths that is substantially dark in an operating environment of the surgical imaging system 500a, or could be operated and/or configured in some other way. In an example, the output of the light source 510a (i.e., the beam of illumination 515a) could be pulsed, and the detector 520a could be operated to generate a first output during a first period of time when the light source 510a is emitting a first amount of illumination and a second output during a second period of time when the light source 510a is emitting a second amount of illumination that is less than the first amount of illumination (e.g., the light source 510a could be emitting substantially no illumination during the second period of time). Spectrographic content of the light received from the portion of tissue 535a could be determined based on a difference, a ratio, or some other relationship between the first and second outputs of the detector 520a. Additionally or alternatively, the light source 510 could be operated to emit illumination at a sufficiently high amplitude that the effects of background illumination (e.g., from ambient light sources in an operating environment of the surgical imaging system 500a) on the operation of the surgical imaging system 500a are minimized.

The surgical imaging system 500a (or other example surgical imaging systems described herein, e.g., 600a, 700a, 800a, 900a) could be operated to determine and/or detect spectrographic content of light received from a plurality of portions of biological tissue. For example, the light source 510a could be operated to illuminate a plurality of portions of tissue (e.g., a set of portions of tissue that are regularly spaced) during a respective plurality of time periods. Correspondingly, the detector 520a could be operated during the plurality of time periods to receive light from respective portions of tissue illuminated by the light source 510a and to determine and/or detect a plurality of spectrographic contents of the received light corresponding to the plurality of portions of tissue.

The wavelength of the illumination emitted by the light source 510a, the specified ranges of wavelengths of light detected by the detector 520a, and other parameters of the surgical imaging system 500a (or other example surgical imaging systems described herein, e.g., 600a, 700a, 800a, 900a) could be chosen relative to an application. For example, the wavelength of illumination emitted by the light source 510a could correspond to an excitation wavelength of a fluorophore in a biological tissue imaged by the surgical imaging system 500a (e.g., a fluorophore introduced into the biological tissue, e.g., to mark a target analyte, e.g., cancer cells). The wavelength of illumination emitted by the light source 510a could be selected to minimize autofluorescence, scattering, or some other optical process(es) in a target tissue.

Information generated by the surgical imaging system 500a (or other example surgical imaging systems described herein, e.g., 600a, 700a, 800a, 900a) could include determined and/or detected spectrographic content for a plurality of portions of a biological tissue, identification information corresponding to the plurality of portions of the biological tissue based on such determined spectrographic content, an image generated based on determined and/or detected spectrographic content and/or identification information. Such information could be used to generate one or more images of the biological tissue, e.g., an image of tissue types of the biological tissue, an image of diseased regions (e.g., cancer-cell-containing regions) of the biological tissue. Such images could be presented to a surgeon (e.g., via a display, a head-mounted display, an augmented reality device, a display of a console used to operate a tele-surgical system) to inform a surgical intervention or other actions of the surgeon. Additionally or alternatively, such images could be used to perform a surgical intervention using an automated surgical system (e.g., to automatically ablate diseased and/or cancerous tissue using a surgical laser).

As shown in FIG. 5A, the detector 520a is not co-axial with the light source 510a. That is, the light source 510a is not located on or substantially proximate to an optical axis of the detector 520a (e.g., an axis passing through the detector 520a and directed toward the center of a field of view of the detector 520a); conversely, the detector 520a is not located on or substantial proximate to an emitted beam axis of the light source 510a (i.e., an axis substantially coincident with the beam of illumination 515a). In some embodiments (e.g., embodiments wherein the detector 520a includes a camera or other light sensitive elements configured to detect the angle or other location information of received light), the detector 520a and light source 510a could be co-axial; that is, the detector 520a and light source 510a could be disposed proximate to each other and/or could share one or more optical elements such that an emitted beam of illumination 515a originates from a point substantially the same as an optical feature (e.g., an aperture) of the detector 520a. In some examples, the surgical imaging system 500a could include a surgical laser configured to emit a beam of light to heat, ablate, or otherwise modify a target portion of biological tissue. Such a surgical laser could be located proximate to and/or share optical elements with (e.g., emit light via actuated mirrors or other light-orientation-controlling elements in common with) the light source 510a such that such that operation of the light source 510a to orient the beam of illumination 515a additionally orients a beam of light emitted by the surgical laser. In some examples, the detector 520a could be located away from an optical axis of the light source 510a and could include a camera or other light sensitive elements configured to detect the angle or other location information of received light; further, such a detector 520a could be operated to determine the location in space of an illumination portion of tissue (relative to the surgical imaging system 500a) in addition to determined spectrographic content of light received from the portion of tissue.

The surgical imaging system 500a (or other example surgical imaging systems described herein, e.g., 600a, 700a, 800a, 900a) or components thereof could be configured to rotate, translate, or otherwise move such that the region imaged by surgical imaging system 500a (i.e., the biological tissue 530a) could be controlled and/or changed. For example, the surgical imaging system 500a could be mounted on a gimbal. Movement of the surgical imaging system 500a could be effected by servos, galvanometers, motors, or some other mechanical actuator(s). In some examples, motions of the surgical imaging system 500a could be controlled to automatically track the biological tissue 530a. In some examples, the surgical imaging system 500a could be manually moved such that a field of view of the surgical imaging system 500a includes a target region (e.g., the biological tissue 530a). For example, the surgical imaging system 500a could be positioned at the beginning of a surgical intervention to image the biological tissue 530a.

A variety of mechanical apparatus could be employed to secure the light source 510a, detector 520a, and other components of the surgical imaging system 500a (or other example surgical imaging systems described herein, e.g., 600a, 700a, 800a, 900a) in place relative to a target region or object (e.g., the biological tissue 530a). For example, the light source 510a, detector 520a, and/or other components could be mounted on a surgical table, a wall, a ceiling, a cart, a wearable device worn by a surgeon or other person, a surgical device or implement (e.g., to the end of a laparoscopic and/or endoscopic instrument), or to some other support. The light source 510a, detector 520a, and/or other components could be part of some other surgical or other apparatus (e.g., an imaging system, a stereotactic surgical system, a robotic surgical system) and could be mounted to a mount, support, or other component(s) of the other surgical or other apparatus. Further, the surgical imaging system 500a could include additional components, e.g., surgical lasers, robotic surgical systems, CT and/or X-ray imagers, MR imagers, ultrasonic imagers, laparoscopic and/or endoscopic systems, and/or other components according to an application. For example, the surgical imaging system 500a could include multiple light sources 510a and/or detectors 520a.

A surgical laser (not shown) included as part of the surgical imaging system 500a (or other example surgical imaging systems described herein, e.g., 600a, 700a, 800a, 900a) or as part of some other surgical instrument or system (e.g., a wholly or partially automated surgical system) could include any device configured to emit a directed beam of light sufficient to cause localized heating of a target region of a biological environment (or some other environment of interest) proximate to where the emitted beam intersects with the biological environment (or other environment of interest). The surgical laser could include a $CO_2$ laser, a semiconductor diode laser, a dye laser, an excimer laser, a fiber laser, a gas laser, a free electron laser, or some other type or types of laser. The surgical laser could include optical elements configured to affect one or more properties of the beam of light emitted by the surgical laser, e.g., lenses, mirrors, diffraction gratings, volume holographic gratings, collimators, nonlinear optical elements (e.g., frequency doubling or tripling media), or other elements. For example, the surgical laser could include a collimator configured to cause the beam of light to have a specified width.

The surgical laser could be configured such that one or more properties of the beam of light have a specified value. For example, the surgical laser could be configured such that a wavelength of the beam of light is a specified wavelength. The specified wavelength could be specified according to an application. For example, the specified wavelength could be an absorption wavelength of hemoglobin such that the beam of light preferentially heats blood. In another example, the specified wavelength could be an absorption wavelength of a contrast agent that is configured to bind to cancer cells such that the beam of light preferentially heats cancer cells and/or tumors. Additionally or alternatively, the specified wavelength could be a wavelength that is not substantially absorbed by a tissue to be spared during a surgical intervention. Other specified wavelengths and/or specified other properties of the beam of light emitted by a surgical laser are anticipated.

In embodiments of the surgical imaging system 500a (or other example surgical imaging systems described herein, e.g., 600a, 700a, 800a, 900a) wherein a surgical laser is included and the surgical laser and light source 510a are co-axial, control of the location of a beam of light emitted by the surgical laser relative to the location of portions of the biological tissue 530a illuminated by the light source 510a could be simplified, taking into account the surgical laser and light source 510a being co-axial. For example, a simple mapping between points in an image generated using the light source 510a and detector 520a and angles of the beam of light emitted by the surgical laser could be determined and used to control the surgical laser such that beam of light is emitted in a direction such that the beam of light interests with the biological tissue 530a at a controlled location that is based on a location of a target determined based on information generated by the detector 520a. Other methods of controlling a surgical laser based on information (e.g., images of the identity of portions of a biological tissue 530a) generated by the surgical imaging system 500a and/or other information are anticipated.

The surgical imaging system 500a (or other example surgical imaging systems described herein, e.g., 600a, 700a, 800a, 900a) could include additional elements or components (not shown). The surgical imaging system 500a could include one or more controllers configured to operate the light source 510a, detector 520a, and/or other elements of the surgical imaging system 500a. The surgical imaging system 500a could include communications devices (wireless radios, wired interfaces) configured to transmit/receive information to/from other systems (e.g., servers, medical imaging devices, surgical implements, surgical robots) to enable functions and applications of the surgical imaging system 500a. For example, the surgical imaging system 500a could include an interface configured to receive imaging information about a target environment of the surgical imaging system 500a (e.g., the biological tissue 530a). The surgical imaging system 500a could include an interface configured to present information about the surgical imaging system 500a to a user and/or to allow the user to operate the surgical imaging system 500a.

Additionally or alternatively, the surgical imaging system 500a (or other example surgical imaging systems described herein, e.g., 600a, 700a, 800a, 900a) could be configured to communicate with another system (e.g., a cellphone, a tablet, a computer, a remote server) and to present a user interface using the remote system. In some examples, the surgical imaging system 500a could be part of another system. For example, the surgical imaging system 500a could be implemented as part of a robotic surgical system (e.g., the light source 510a, detector 520a, and other components (e.g., surgical laser(s)) configured as described herein could be disposed as part of a robotic surgical system and could be operated as described herein). In some examples, the surgical imaging system 500a could include multiple light sources 510a, multiple detectors 520a, or other additional components. The surgical imaging system 500a could include sensors and/or be in communication with sensors configured to image other properties of a target environment (e.g., the biological tissue 530a). Other configurations, operations, and applications of surgical imaging systems as described herein are anticipated.

Note that the configuration and/or operation of the light source 510a to illuminate a portion of a surgical environment with a spot of monochromatic illumination is intended as a non-limiting example. Alternatively, a larger and/or differently-shaped region of the surgical environment (e.g., a line within the surgical environment; substantially the entire surgical environment and/or the entire surgical environment within a field of view of the surgical imaging system) could be illuminated by a light source of a surgical imaging system. Further, a light source could emit illumination at a controllable wavelength (e.g., illumination that is substantially monochromatic, but having a wavelength that can be altered by operation of the light source) and/or at a range of wavelengths (e.g., a broadband source that emits light across some specified range of wavelengths).

Similarly, the detector of a surgical imaging system could include individual light-sensitive elements configured to detect light within a particular specified narrow range of wavelengths (e.g., by including a filter, a prism and other optics, and/or having an intrinsic sensitivity to the light across the range of wavelengths) or configured to be sensitive to a broad range of wavelengths of light (e.g., broadband light-sensitive elements). Further, such a detector could include a camera or other elements configured to receive and detect properties of light from a plurality of separate regions of a surgical environment simultaneously, or could include light sensitive elements configured to receive light from an entire field of view of the surgical environment and to provide a single output related to the received light (similar to the detector 520a of the first example surgical imaging system 500a).

Figure 6A:
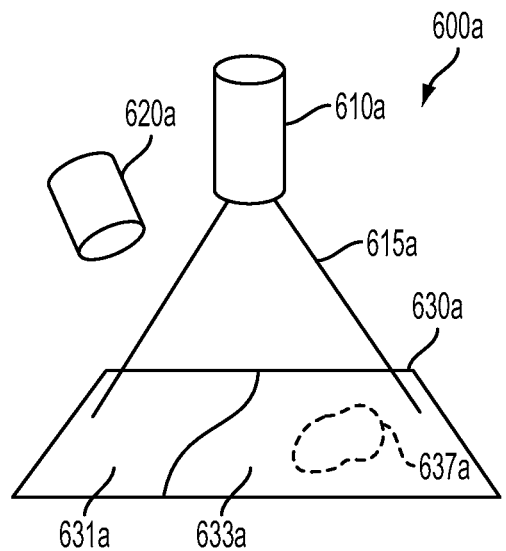
FIG. 6A illustrates an example system imaging a surgical environment.

In some examples, a surgical imaging system could include a light source configured to illuminate an area of a surgical environment with light at a plurality of respective different wavelengths. FIG. 6A illustrates elements of a second example surgical imaging system 600a including a light source 610a and a detector 620a. The light source 610a is configured to emit illumination 615a containing light at a plurality of specified wavelengths during a respective plurality of periods of time to illuminate a field of view of a surgical environment containing a biological tissue 630a. The biological tissue 630a includes a first muscle 631a and a second muscle 633a. The detector 620a is configured to receive light from the field of view containing the biological tissue 630a and to generate a plurality of images of the field of view corresponding to the illumination of the biological tissue 630a by the light of the respective plurality of different wavelengths during the respective plurality of periods of time. From the plurality of images, information about the spectrographic contents of the received light can be determined. The second muscle 633a includes a tagged region 637a containing marker (e.g., a dye or chromophore) configured to selectively interact with an analyte that is present in the tagged region 637a.

The light source 610a could include a tunable laser controllable to emit light at any of a plurality of different wavelengths (e.g., wavelengths ranging between approximately 400 nanometers and approximately 2.5 micrometers). Such a tunable laser could include an excimer laser, a dye laser, a $CO_2$ laser, a free-electron laser, or some other laser element configured to emit light at a plurality of different, controllable wavelengths. In some examples, the wavelength of the light emitted by such a tunable laser could be controlled by controlling a geometry or size of one or more elements (e.g., a reflector, a resonating cavity) of the tunable laser. In some examples, a Bragg reflector or other element of the tunable laser could be rotated or otherwise actuated to control the wavelength of light emitted by the tunable laser. In some embodiments, the light source 610a could include a plurality of lasers configured to emit light at wavelengths corresponding to respective different wavelengths, and operation of the light source 610a to emit light of a particular wavelength could include operating the corresponding laser of the light source 620a to emit light at the controlled wavelength. Other configurations and operations of a tunable laser are anticipated.

The detector 620a could include a camera configured to detect the amplitude or other properties of light received by the detector 620a across a broad range of wavelengths (e.g., across the range of wavelengths of light that can be emitted by the tunable laser). That is, the detector 620a could be configured to act as broadband monochrome camera, receiving light from the biological tissue 630a during a plurality of periods of time and outputting a respective plurality of images related to the absorption or other interactions of the biological tissue 630a with light of a corresponding plurality of wavelengths emitted by the light source 610a during a the respective plurality of periods of time. This could include the detector 620a containing a regular two-dimensional (or otherwise arranged) array of light sensitive elements (e.g., photodiodes, phototransistors, pixels of a charge-coupled device (CCD), active pixel sensors) configured such that the output of an individual light sensitive element is related to the amplitude of the light received by the detector 620a from a particular direction (corresponding to a particular portion of the biological tissue 630a). Spectrographic content of light received from a particular portion of the biological tissue 630a could be determined based on a plurality of detected amplitudes (or other properties of light) detected by a particular pixel (or other light sensitive element) of the detector 620a corresponding to the particular portion of the biological environment 630a during the respective plurality of periods of time and corresponding to receptive wavelengths of illumination emitted by the light source 610a. Other configurations of the detector 620a to enable the detection and/or determination of the spectrographic content of light received by the detector 620a are anticipated.

Figure 6B:
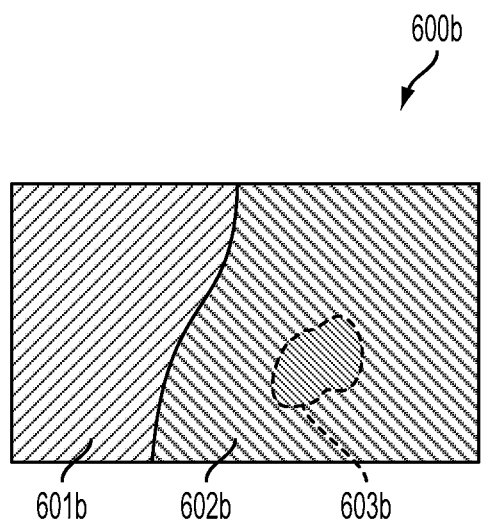
FIG. 6B illustrates an example image of the surgical environment of FIG. 6A obtained by the system of FIG. 6A.

Spectrographic content of light received by the surgical imaging system 600a from a portion of a surgical environment (e.g., from the biological tissue 630a) could take the form of a plurality of images of the light received from the biological tissue 630a. An example of such an image is illustrated in FIG. 6B. The example image 600b illustrates the amplitude of light received from regions of the biological tissue 630a in response to illumination of the biological tissue 630a by light at a particular wavelength as emitted by the light source 610a during a period of time corresponding to the period of time during which the image 600b is taken. So, the image 600b includes first 601b, second 602b, and third 603b image regions corresponding to light received from the first muscle 631a, and tagged region 637a of the second muscle 602b, respectively. Spectrographic content (or other information) about light received from a particular portion of the biological tissue 630a could be determined based on an amplitude or other image data from a particular pixel of the image 600b, and of a plurality of additional image (not shown) taken when the biological tissue is illuminated by a respective plurality of different wavelengths of light by the light source 610a, where the particular pixel is positioned to receive light from the particular portion of the biological tissue 630a. Such spectrographic content could be determined for a plurality of pixels and/or corresponding portions of the biological tissue based on the plurality of taken images.

Figure 7A:
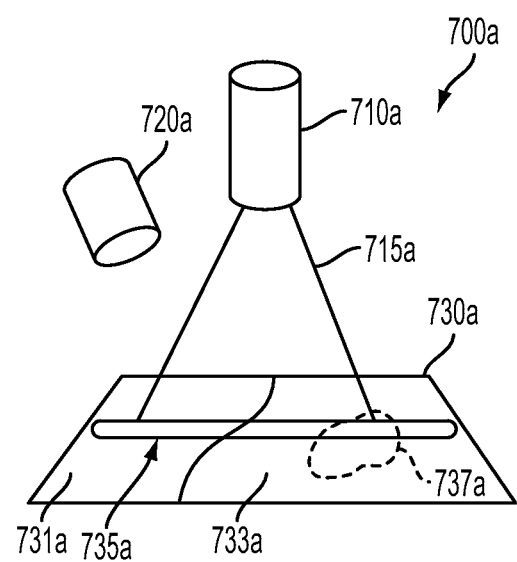
FIG. 7A illustrates an example system imaging a surgical environment.

A light source of a surgical imaging system could include optics or other elements configured to emit a beam of light configured to illuminate a line-shaped region of a target surgical environment, and to scan such a surgical environment by scanning the emitted beam of light across the target surgical environment. FIG. 7A illustrates elements of a third example surgical imaging system 700a including a light source 710a and a detector 720a. The light source 710a is configured to emit a beam of illumination 715a containing light at a specified wavelength and to illuminate a line 735a on the biological tissue 730a. The biological tissue includes a first muscle 731a and a second muscle 733a. The detector 720a is configured to receive light from an area of the biological tissue 730a and to generate information about the spectrographic contents of the received light. The second muscle 733a includes a tagged region 737a containing an optical marker (e.g., a chromophore, a fluorophore) configured to selectively interact with an analyte that is present in the tagged region 737a.

The light source 710a could include a variety of light-emitting elements configured to produce light at substantially one wavelength (i.e., containing light of wavelengths within a specified narrow range of wavelengths). This could include lasers, light-emitting diodes (LEDs), or other substantially monochromatic light sources. Additionally or alternatively, the light source 710a could include a light emitting element that emits light across a wider range of wavelengths, and this non-monochromatic light could be emitted through one or more filters (e.g., filters including one or more Bragg reflectors, prisms, diffraction gratings, slit apertures, monochromators) configured to only allow the transmission of light within a narrow range of wavelengths. The light source 710a could include mirrors, lenses, diffraction gratings, or other optics controlled by galvanometers, motors, or other actuators to control the direction of the beam of illumination 715a such that the location of an illuminated line of the surgical environment 730a could be controlled (e.g., by a controller operably coupled to the light source 710a).

The detector 720a could include a plurality of light-sensitive elements configured to detect the amplitude or other properties of light received by the detector 720a within one or more respective ranges of wavelengths from respective particular portions of the illuminated line 735a of the biological tissue 730a. That is, the detector 720a could be configured to act as a hyperspectral imager, receiving light from the line 735a of the biological tissue 730a in sync with the illumination of the line 735a of the biological tissue 730a by the light source 710a and outputting information related to a plurality of spectra of the received light (i.e., outputting information relating to a plurality of spectrographic contents of the received light) corresponding to the plurality of portions within the line 735a of the biological tissue 730a. This could include the detector 720a containing a prism, aperture, actuated optics (e.g., mirrors, lenses) and a two-dimensional array of light sensitive elements (e.g., photodiodes, phototransistors, pixels of a charge-coupled device (CCD), active pixel sensors) configured such that the output of an individual light sensitive element is related to the amplitude of the light received from a particular portion of the line 735a and within a specified range of wavelengths. Other configurations of the detector 720a to enable the detection and/or determination of spectrographic content of light received by the detector 720a from a plurality of portions of a surgical environment are anticipated.

Spectrographic content or other optical information generated by a surgical imaging system could be relative (i.e., having an amplitude or other property defined in terms of some other amplitude or variable generated and/or detected by the surgical system) or absolute (i.e., having an amplitude or other property defined in terms of some calibrated physical baseline). In some embodiments, the surgical imaging system could be operated to calibrate one or more elements of the surgical imaging system. For example, the surgical imaging system could be operated to generate spectrographic content or other information related to a calibration object having one or more known optical and/or spectrographic properties (e.g., a uniform reflectivity as a function of wavelength across a specified range of wavelengths) and a difference and/or correspondence between the spectrographic content or other information and the known optical and/or spectrographic properties could be used to correct subsequent spectrographic content or other information generated by the surgical imaging system.

Such a calibration object could be flat (e.g., could take the form a sheet or plate configured to be placed on tissue or other elements of a surgical environment) or could have some other shape (e.g., a sphere, a cube, a rod). A calibration object could be attached to an armature or to a surgical object (e.g., a retractor) within the surgical environment. Additionally or alternatively, a calibration object could be attached and/or mounted to a light source and/or detector of the surgical imaging system. In some examples, the calibration object could be internal to the surgical imaging system; for example, light emitted by the light source could be directed within the surgical imaging system (e.g., along a calibration light path) to illuminate the calibration object, and light emitted from the calibration object in response to such illumination could be directed to one or more light-sensitive elements of the detector of the surgical imaging system. The calibration object could be a black object (e.g., absorbing substantially all illumination across a range of wavelengths), a white object (e.g., absorbing substantially no illumination across a range of wavelengths), a colored object (e.g., absorbing substantially all illumination outside of a specified narrow range of wavelengths), or could have some other specified and/or determined wavelength-dependent optical property.

Figure 8A:
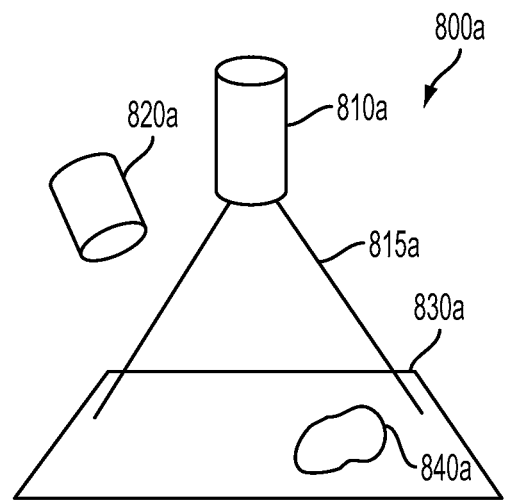
FIG. 8A illustrates an example system imaging a surgical environment.

As an example, FIG. 8A illustrates elements of a fourth example surgical imaging system 800a including a light source 810a and a detector 820a. The light source 810a is configured to emit a beam of illumination 815a containing light at one or more specified wavelengths during one or more periods of time and to illuminate a surgical environment 830a. The surgical environment 830a includes a calibration object 840a. The detector 820a is configured to receive light from the surgical environment 830a and to generate information about the spectrographic contents of the received light.

Figure 8B:
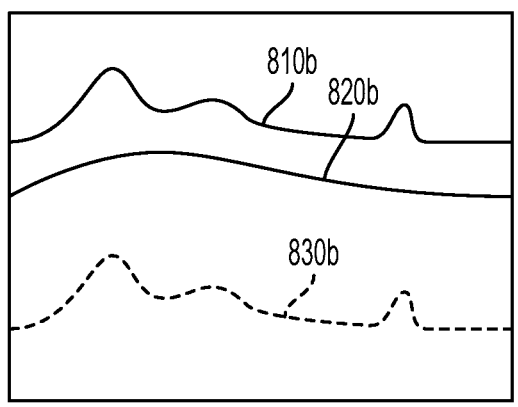
FIG. 8B illustrates example spectrographic content of light received from portions of the surgical environment of FIG. 8A by the system of FIG. 8A.

Example baseline spectrographic content 820b corresponding to the spectrographic content of light received from the calibration object 840a is illustrated in FIG. 8B. FIG. 8B additionally includes uncorrected spectrographic content 810b corresponding to the spectrographic content of light received from another, non-calibration portion of the surgical environment 830a. The horizontal axis indicates wavelength (increasing to the right) and the vertical axis indicates amplitude. Corrected spectrographic content 830b corresponding to the non-calibration portion of the surgical environment 830a could be determined by determining a difference between the baseline spectrographic content 820b and the uncorrected spectrographic content 810b. Additionally or alternatively, corrected spectrographic content for a particular portion of the surgical environment could be determined based on a ratio, logarithmic function, nonlinear function power function, product, exponential, or some other operation or combination of operations of uncorrected spectrographic content for the particular portion and baseline spectrographic content corresponding to a calibration object.

The calibration object 840a could be an object having a known and/or stable emission, reflection, absorption, excitation, or other spectrum. The known spectrographic properties of the calibration object could be specified (i.e., selected by the composition and/or manufacture of the object) and/or could be measured (e.g., by a laboratory spectrometer or other optical measurement device). The composition and/or manufacture of the calibration object could be specified to have a particular uniform reflectivity or other optical property across a wide range of wavelengths. The composition and/or manufacture of the calibration object could be specified to have a particular reflectivity or other spectrum having one or more peaks to enable calibration of the wavelength of light emitted by a tunable laser of other optical device.

Other methods of configuring and/or operating a light source, detector, and/or other elements of a surgical imaging system (e.g., to identify one or more portions of a surgical environment, to ablate or otherwise interact with the portion of the surgical environment based on such identification) are anticipated.

IV. Example Surgical Imaging System

Figure 9:
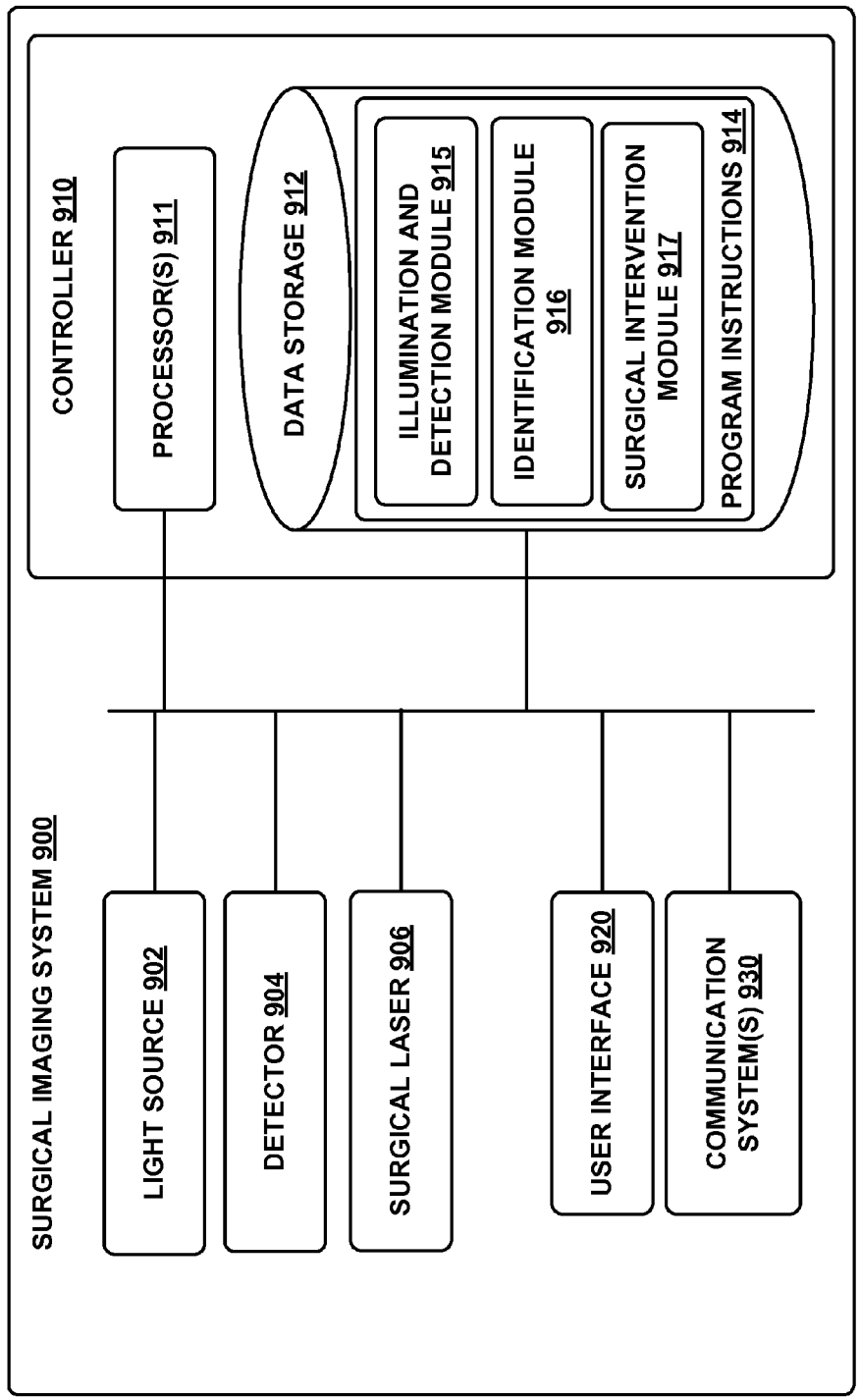
FIG. 9 is a functional block diagram of an example imaging system.

FIG. 9 is a simplified block diagram illustrating the components of a surgical imaging system 900, according to an example embodiment. Surgical imaging system 900 may take the form of or be similar to one of the example surgical imaging systems 500a, 600a, 700a, 800a shown in FIGS. 5A, 6A, 7A, and 8A. Surgical imaging system 900 may take a variety of forms, such as a wall, surgical table, ceiling, or floor-mounted device. Surgical imaging system 900 could also take the form of a system, device, or combination of devices that is configured to part of another device, apparatus, or system. For example, surgical imaging system 900 could take the form of a light source, detector, and other components configured to be mounted to or otherwise disposed as part of a surgical apparatus, tool, implement, or system (e.g., a robotic surgical system, a stereotactic surgical apparatus, an imaging-guided surgical system). Surgical imaging system 900 could also take the form of a system configured to illuminate and to receive light from some other industrial environment, medical environment, scientific environment, or some other environment. Surgical imaging system 900 also could take other forms.

In particular, FIG. 9 shows an example of a surgical imaging system 900 having a light source 902, a detector 904, a surgical laser 906, a user interface 920, communication system(s) 930 for transmitting data to a remote system, and controller 910. The components of the surgical imaging system 900 may be disposed on or within a mount or housing or on some other structure for mounting the system to enable stable imaging or other functions relative to elements in a surgical environment of interest, for example, to a surgical frame secured relative to a biological tissue subject to a surgical intervention. The surgical imaging system 900 could include additional components, for example, an actuated retractor, an actuated scalpel or electosurgical instrument, or some other surgical instrument or other component(s) according to an application.

Controller 910 may be provided as a computing device that includes one or more processors 911. The one or more processors 911 can be configured to execute computer-readable program instructions 914 that are stored in a computer readable data storage 912 and that are executable to provide the functionality of a surgical imaging system 900 as described herein.

The computer readable data storage 912 may include or take the form of one or more non-transitory, computer-readable storage media that can be read or accessed by at least one processor 911. The one or more computer-readable storage media can include volatile and/or non-volatile storage components, such as optical, magnetic, organic or other memory or disc storage, which can be integrated in whole or in part with at least one of the one or more processors 911. In some embodiments, the computer readable data storage 912 can be implemented using a single physical device (e.g., one optical, magnetic, organic or other memory or disc storage unit), while in other embodiments, the computer readable data storage 912 can be implemented using two or more physical devices.

The light source 902 is configured to illuminate one or more portions of a surgical environment with illumination at one or more specified wavelengths. The one or more portions of the surgical environment could comprise a spot, line, and/or some otherwise-shaped region of the surgical environment (e.g., substantially the entire surgical environment and/or the entire surgical environment within a field of view of the surgical imaging system 900). Further, the light source 902 could emit illumination at a fixed wavelength, a controllable wavelength (e.g., illumination that is substantially monochromatic, but having a wavelength that can be altered by operation of the light source) and/or at a range of wavelengths (e.g., a broadband or white illumination source across some specified range of wavelengths). The direction of illumination emitted by the light source 902 (and thus the location of any portion(s) of the surgical environment illuminated by the light source 902) could be controlled by one or more actuator(s) 908 configured to actuate one or more mirrors, lenses, diffraction gratings, or other optical elements optically coupled to the light source 902.

The detector 904 includes a plurality of individual light-sensitive elements configured to detect light within a particular specified narrow range of wavelengths (e.g., by including a filter, a prism and other optics, and/or having an intrinsic sensitivity to the light across the range of wavelengths) and/or configured to be sensitive to broad range of wavelengths of light (e.g., broadband light-sensitive elements). Further, individual light-sensitive elements of the detector 904 could be configured to receive and detect properties of light from respective portions of a surgical environment, or could be configured to receive light from an entire field of view of the surgical environment and to provide a single output related to the received light (similar to the detector 520a of the first example surgical imaging system 500a). In some examples, the location of a portion of a surgical environment from which the detector 904 is configured to received light could be controlled by one or more mirrors, prisms, or other actuated optical elements (e.g., the detector 904 could be configured and operated as a line-scanning hyperspectral imager).

The surgical laser 906 could is configured to emit a directed beam of light sufficient to cause localized heating of a target portion of an environment of interest (e.g., a biological tissue subject to a surgical intervention) proximate to where the emitted beam intersects with the environment of interest. The surgical laser 906 could include a 2 micron laser, a $CO_2$ laser, a semiconductor diode laser, a dye laser, an excimer laser, a fiber laser, a gas laser, a free electron laser, or some other type or types of laser. The surgical laser 906 could include optical elements configured to affect one or more properties of the beam of light emitted by the surgical laser, e.g., lenses, mirrors, diffraction gratings, volume holographic gratings, collimators, nonlinear optical elements (e.g., frequency doubling or tripling media), or other elements.

The program instructions 914 stored on the computer readable data storage 912 may include instructions to perform any of the methods described herein. For instance, in the illustrated embodiment, program instructions 914 include an illumination and detection module 915, an identification module 916, and a surgical intervention module 917.

The illumination and detection module 915 can include instructions for operating the light source 902, detector 904, and/or actuator(s) 908 to enable any of the functions or applications of a surgical imaging system to determine and/or detect spectrographic information and/or content corresponding to more or more portions of a surgical environment as described herein. Generally, instructions in the illumination and detection module 915 describe methods of operating the light source 902 and/or actuator(s) 908 to illuminate one or more portions of a surgical environment with light at one or more specified wavelengths during one or more respective periods of time. Instructions in the illumination and detection module 915 further describe methods of operating the detector 904 to receive light from illumination portions of the surgical environment and to determine spectrographic content for a particular portion of the surgical environment based on the light received from the particular portion of the surgical environment. Other operations, functions, and applications of the light source 902, detector 904, actuator(s) 908, and/or of other components of the surgical imaging system 900 as described herein could be implemented as program instructions in the illumination and detection module 915.

The identification module 916 can include instructions for identifying a particular portion of the surgical environment based on spectrographic content determined from light received from the portion of the surgical environment. The instructions could include instructions to implement a variety of classifiers and/or combinations of classifiers to identify or otherwise assign a classification to the portion of a surgical environment based on the spectrographic contents of light received from the portion. Implemented classifiers could generate a binary output (e.g., "biological tissue" vs. "not biological tissue") or an output having a plurality of possible states (e.g., "artery," "vein," "nerve," "tendon," "skin," "muscle," "liver," "kidney," "pancreas," "fat," "necrosis," "tumor"). A plurality of possible outputs states could be nominal (i.e., categorical and non-ordered) or ordinal (e.g., "very unlikely to contain cancer cells," "slightly unlikely to contain cancer cells," "slightly likely to contain cancer cells," "very likely to contain cancer cells"). Output of a classifier corresponding to a particular portion of a surgical environment could be based only on spectrographic content from the particular portion or could be based additionally on spectrographic content from other portions of the surgical environment (e.g., neighboring portions of the surgical environment to enable a spatially smooth output of the classifier across portions; a portion of the surgical environment containing a calibration object having known spectrographic properties to act as a baseline for comparison). A classifier could generate multiple outputs for a single portion (e.g., could output one of "biological tissue" and "surgical instrument" and one of "contains fluorophore" and "does not contain fluorophore").

Classifiers implemented by a controller could include linear classifiers, nonlinear classifiers, support vector machines, decision trees, k-nearest-neighbors, neural networks, thresholds, or other classifiers and/or combinations thereof. Further, a controller could perform some preprocessing on input spectrographic content before the application of a classifier. For example, input content could be subject to some transformation (e.g., conversion by application to a logarithmic, hyperbolic, power series, or other nonlinear function), dimensionality reduction (e.g., principal components analysis, factor analysis, independent components analysis, isomap, linear discriminant analysis, non-negative matrix factorization), filtering (e.g., spatial filtering across spectrographic contents for neighboring portions, wavelength filtering to smooth a determined spectrum) or some other preprocessing step.

The surgical intervention module 917 can include instructions for planning and/or executing one or more surgical interventions on a biological tissue based on information identifying particular portions of a surgical environment containing the biological tissue. The instructions could include instructions to determine a location, extent, or other properties of an identified target tissue (e.g., an extent of a tumor containing a cancerous target tissue). Instructions of the surgical intervention module 917 can further include instructions for controlling one or more surgical instruments (e.g., the surgical laser 906, an actuated scalpel, an actuated retractor) to effect one or more surgical interventions on the biological tissue. For example, the surgical intervention module 917 can include instructions for operating the surgical laser 906 (e.g., controlling a wavelength, energy level, direction or other properties of the light emitted by the surgical light 906) according to a determined location, extent, or other properties of an identified target tissue such that the identified target tissue is ablated (e.g., such that a tumor containing cancerous target tissue is ablated).

Some of the program instructions of the illumination and detection module 915, identification module 916, and/or surgical intervention module 917 may, in some examples, be stored in a computer-readable medium and executed by a processor located external to the surgical imaging system 900. For example, the surgical imaging system 900 could be configured to illuminate and to received light from a portion of a biological environment and then transmit related data to a remote server, which may include a mobile device, a personal computer, the cloud, or any other remote system, for further processing (e.g., for the determination of spectrographic content of the received light, for identifying the portion of the surgical environment based on the determined spectrographic content).

User interface 920 could include indicators, displays, buttons, touchscreens, head-mounted displays, displays of a console of a tele-surgical system, and/or other elements configured to present information about the surgical imaging system 900 to a user and/or to allow the user to operate the surgical imaging system 900. Additionally or alternatively, the surgical imaging system 900 could be configured to communicate with another system (e.g., a cellphone, a tablet, a computer, a remote server) and to present elements of a user interface using the remote system. The user interface 920 could be disposed proximate to the light source 902, detector 904, surgical laser 906, controller 910, or other elements of the surgical imaging system 900 or could be disposed away from other elements of the surgical imaging system 900 and could further be in wired or wireless communication with the other elements of the surgical imaging system 900. The user interface 920 could be configured to allow a user to specify some operation, function, or property of operation of the surgical imaging system 900. The user interface 920 could be configured to present information about a biological tissue or other contents of the surgical environment (e.g., a tissue type, a presence of fluorophore) to the user using a display, to present a degree of progress of an ongoing function of the surgical imaging system (e.g., a degree of progress in ablating biological tissue along a specified trajectory using a surgical laser of the surgical imaging system 900), to present an image of a biological tissue or other contents of the surgical environment generated using the light source 902 and detector 904, or using some other imaging component or sensor, or to present some other information to a user. Other configurations and methods of operation of a user interface 920 are anticipated.

Communication system(s) 930 may also be operated by instructions within the program instructions 914, such as instructions for sending and/or receiving information via a wireless antenna, which may be disposed on or in the surgical imaging system 900. The communication system(s) 930 can optionally include one or more oscillators, mixers, frequency injectors, etc. to modulate and/or demodulate information on a carrier frequency to be transmitted and/or received by the antenna. In some examples, the surgical imaging system 900 is configured to indicate an output from the controller 910 by transmitting an electromagnetic or other wireless signal according to one or more wireless communications standards (e.g., Bluetooth, WiFi, IRdA, ZigBee, WiMAX, LTE). In some examples, the communication system(s) 930 could include one or more wired communications interfaces and the surgical imaging system 900 could be configured to indicate an output from the controller 910 by operating the one or more wired communications interfaces according to one or more wired communications standards (e.g., USB, FireWire, Ethernet, RS-232).

The computer readable data storage 912 may further contain other data or information, such as medical and health history of a patient whose biological tissue is being imaged or otherwise interacted with by the surgical imaging system 900, that may be useful in tracking or otherwise interacting with a biological tissue or other environment of interest. Further, the computer readable data storage 912 may contain data corresponding to imaging information about a biological tissue or other environment of interest. The computer readable data storage 912 may contain calibration data corresponding to a configuration of the surgical imaging system 900, a calibration object, or some other information. Calibration, model, imaging, and/or other data may also be generated by a remote server and transmitted to the surgical imaging system 900 via communication system(s) 930.

In some examples, the collected calibration and/or model data, stored information about operation of the surgical imaging system 900 (e.g., information about identification of biological tissues or other contents of a surgical environment performed using the surgical imaging system 900), health state information (e.g., health state of biological tissues) detected by the surgical imaging system 900 and other usage or other information may additionally be input to a cloud network (e.g., using the communications system(s) 930) and be made available for download by users having sufficient permissions (e.g., a surgeon tasked with reviewing the outcome of a surgical intervention wholly or partially effected using the surgical imaging system 900). Other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring outcomes of a surgical intervention or other treatment. For example, high-density, real-time data may be collected from a population of device users who have experienced a surgical intervention implemented using information generated by the surgical imaging system 900 to assess the safety and efficacy of the surgical intervention. Such data may also be used on an individual level to assess a particular patient's response to a surgical intervention or therapy. Based on this data, a physician or clinician may be able to tailor a future surgical intervention or other treatment to suit an individual's needs.

V. Example Methods

Figure 10:
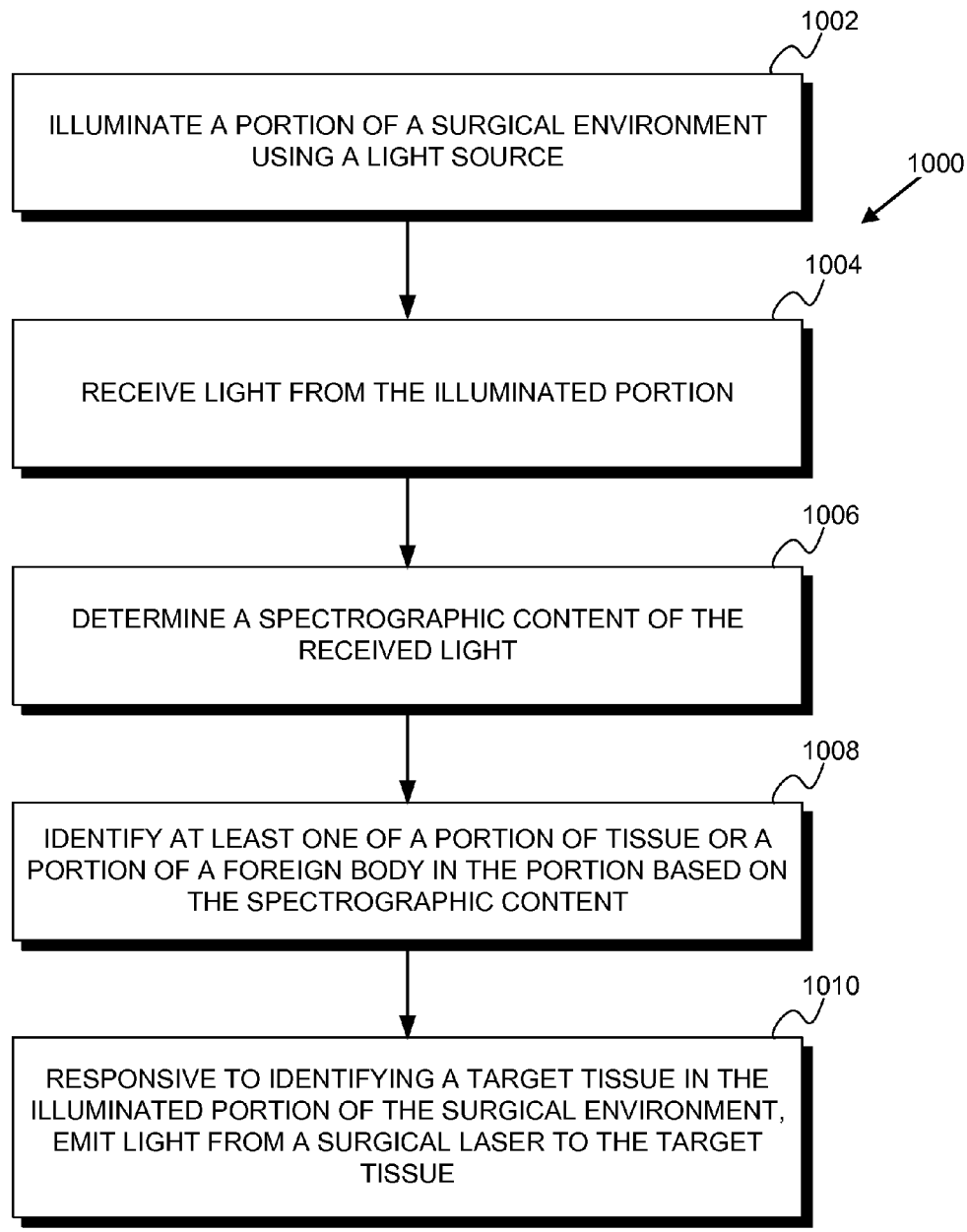
FIG. 10 is a flowchart of an example method.

FIG. 10 is a flowchart of an example method 1000 for operating elements of a surgical imaging system to perform functions and/or applications of the surgical imaging system. The surgical imaging system includes a light source configured to illuminate one or more portions of a surgical environment, where the surgical environment contains a tissue subject to a surgical intervention involving one or more surgical instruments (e.g., a scalpel, a surgical laser, an RF or electrical cautery or ablation tool, a retractor, a hemostat). The surgical imaging system also includes a detector configured to receive light from the illuminated one or more portions of the surgical environment and to generate an output such that a spectrographic content of the received light can be determined. The surgical imaging system further includes a surgical laser configured to emit light sufficient to ablate, cauterize, or otherwise modify biological tissues.

The method 1000 includes operating the light source to illuminate a portion of the surgical environment (1002). This could include operating a light-emitting element (e.g., a laser) of the light source to illuminate the portion of the surgical environment with light at a particular fixed wavelength. This (1002) could include operating tunable laser of the light source to illuminate the portion of the surgical environment with light at a plurality of different wavelengths during a respective plurality of periods of time. This (1002) could include operating an actuator to control the configuration of a mirror, lens, or other optical element(s) to control the direction of a beam of light emitted by the light source to illuminate a spot, line, or other region of the surgical environment containing the portion of the surgical environment.

The method 1000 additionally includes receiving light from the illuminated portion of the surgical environment (1004). This could include operating a detector of the surgical imaging system to output a set of detected amplitudes or other properties of light received by the detector within one or more respective ranges of wavelengths. That is, the detector could be configured to act as a spectrometer, receiving light from the surgical environment and outputting information related to the spectrum of the received light (i.e., outputting information relating to the spectrographic content of the received light). Additionally or alternatively, this (1004) could include operating a detector of the surgical imaging system to output a set of detected amplitudes or other properties of light received by the detector during a plurality of periods of time in response to the illumination of the surgical environment by a light source with light at a respective plurality of different wavelengths. Further, receiving light from the illuminated portion of the surgical environment (1004) could include imaging the surgical environment.

The method 1000 additionally includes determining a spectrographic content of the received light (1006). This could include receiving from a detector (e.g., a spectrometer, a hyperspectral imager) a set of detected amplitudes or other properties of the received light within one or more respective ranges of wavelengths. This (1006) could include determining spectrographic content based on a plurality of detected amplitudes (or other properties of light) detected by a particular pixel (or other light sensitive element) of a detector during a respective plurality of periods of time and corresponding to a respective plurality of different wavelengths of light illuminating the portion of the surgical environment. Determining a spectrographic content of the received light (1006) could include spatially (i.e., across received lights and/or determined spectrographic content thereof corresponding to proximate portions of the surgical environment), temporally (i.e., across lights received at two or more points in time), by wavelength, or otherwise filtering and/or preprocessing determined spectrographic content. In some examples, determining a spectrographic content of the received light (1006) could include determining one or more properties (e.g., an amplitude, a center wavelength, a peak width) of one or more features (e.g., a peak, a trough, a pass band, a slope or other rate of change of amplitude according to wavelength within one or more ranges of wavelengths) of a detected and/or determined spectrum of the received light.

The method 1000 additionally includes identifying at least one of a portion of tissue or a portion of a foreign body in the portion of the surgical environment based on the determined spectrographic content (1008). This could include determining that the portion of the surgical environment contains biological tissue, that the portion contains biological tissue of a particular type (e.g., "muscle," "skin," "blood vessel," "nerve," "tumor," "tendon"), and/or that the portion contains an amount of a particular chromophore fluorophore, or other marking agent. This (1008) could include determining that the portion of the surgical environment contains portion of a surgical instrument, a portion of a particular type of surgical instrument (e.g., "retractor," "hemostat," "stainless steel instrument," "plastic retractor," "titanium instrument," "instrument contaminated or marked with a particular chromophore, fluorophore, or other marking agent"), a foreign body, and/or a particular type of foreign body (e.g., "suture," "nylon suture," "silk suture," "surgical staple," "implant device," "electrode lead," "drain catheter," "surgical mesh"). Identifying at least one of a portion of tissue or a portion of a foreign body in the portion of the surgical environment (1008) could include implementing a classifier and/or combination of classifiers to identify or otherwise assign a classification to the portion of the surgical environment based on the determined spectrographic content. Implementing a classifier could include generating a binary output (e.g., "biological tissue" vs. "not biological tissue") or an output having a plurality of possible states (e.g., "artery," "vein," "nerve," "tendon," "skin," "muscle," "fat," "necrosis," "tumor").

The method 1000 additionally includes, responsive to identifying a target tissue in the illuminated portion of the surgical environment, emitting light from the surgical laser to the target tissue (1010). This could include emitting a beam of light to ablate, dissect, cauterize, or otherwise damage or destroy the target tissue. Emitting light from the surgical laser to the target tissue (1010) could include operating a 2 micron laser, $CO_2$ laser, an excimer laser, or some other variety of laser configured to apply energy to biological tissue sufficient to ablate or otherwise modify the biological tissue. Emitting light from the surgical laser to the target tissue (1010) could include operating optics of the surgical laser to control a direction and/or focus of the beam of light emitted by the surgical laser and/or operating an armature on which the surgical laser is disposed to control the location and/or orientation of the surgical laser.

The method 1000 could include additional steps. For example, the method could include illuminating, receiving light from, determining spectrographic content of the received light, and identifying a plurality of portions of the surgical environment. In some examples, the method 1000 could include implementing one or more surgical interventions in a wholly or partially automated manner based on identification or other information determined about a portion of the surgical environment. For example, identifying at least one of a portion of tissue or a portion of a foreign body in the portion of the surgical environment (1008) could include identifying a target tissue and, responsive that this identification, effecting one or more surgical interventions on the target tissue using a robotic surgical system (e.g., excision by an actuated scalpel, thermal, RF, and/or electrical ablation of a tissue, cauterization of a wound and/or target vascular tissue).

The method 1000 could further include calibrating one or more elements of the surgical imaging system. For example, a calibration object having one or more known optical and/or spectrographic properties could be present in the surgical environment (or some other environment accessible to the surgical imaging system). The surgical imaging system could illuminate, receive light from, and determine spectrographic content of the received light to determine calibration data (e.g., a baseline spectrum) for the surgical imaging system. Subsequently, the surgical imaging system could use the determined calibration data to offset, scale, or otherwise adjust spectrographic content determined based on received light from portions of the surgical environment.

The method 1000 could include other additional steps or elements. The method 1000 could include any additional steps, or could include details of implementation of the listed steps 1002, 1004, 1006, 1008 or of other additional steps, as described herein in relation to the operation of a surgical imaging system. Additional and alternative steps of the method 1000 are anticipated.

In some examples, the surgical environment described in relation to the method 1000 above could contain a biological tissue of a human body. For example, the environment could contain a tissue that has been determined to include a tumor that could be resected, ablated, or otherwise removed to change and/or affect a health state of the human body. Other examples of surgical environments, biological tissues, surgical interventions, surgical instruments, foreign bodies, methods of operating a surgical imaging system, configurations of surgical imaging systems, and other elements are anticipated.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, information about a surgical intervention performed on the user, information about biological tissues of a user, a user's preferences, or a user's current location), or to control whether and/or how to receive content from a content server (e.g., a profile of power to ablate a tissue applied using a heating laser) that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a hospital, city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to image and/or manipulate biological environments (e.g., tissues) of a human body, it is noted that the disclosed devices, systems, and methods can be applied in other contexts as well. For example, imaging and/or ablation systems configured as disclosed herein may be included as part of other surgical and/or medical imaging apparatus. In some contexts, such an imaging system could be operated to detect one or more properties of a tissue or other element of a human body, possibly in concert with other medical imaging or other sensor apparatus. In another example, an imaging system could be configured to image and/or ablate specified elements and/or regions of a non-tissue element of a human body. For example, the imaging system could be configured and/or applied to image specified regions of an implantable device (e.g., a stent, an artificial joint, a pacemaker) to control the effecting of a desired change in the implantable device (e.g., to section the device, to weld an element of the device, to activate an element of the device, to trim an element (e.g., an electrode) of the device).

In other examples, devices, systems, and methods disclosed herein may be applied to image and/or ablate regions of environments that are not in or on a human body. For example, imaging systems disclosed herein may be included in systems used to image and/or ablate specified regions (e.g., tissues) of an animal. In another example, devices, systems, and methods disclosed herein may be applied to image and/or ablate regions of an industrial environment or a work element of an industrial process, such as a work element in a laser cutting process.

Additionally, while various aspects and embodiments have been disclosed herein, other aspects and embodiments will be apparent to those skilled in the art. The various aspects and embodiments disclosed herein are included for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   a light source;
   a detector;
   a surgical laser; and
   a controller operatively coupled to the light source, the detector, and the surgical laser, wherein the controller comprises a computing device programmed to perform operations comprising:
      controlling the light source to illuminate a portion of a surgical environment, wherein the surgical environment comprises a tissue subject to a surgical intervention involving one or more surgical instruments;
      controlling the detector to obtain a spectrographic content of light received by the detector from the illuminated portion of the surgical environment;
      determining whether the illuminated portion of the surgical environment contains a portion of a non-biological foreign body based on the spectrographic content of the received light; and
      in response to a determination that the illuminated portion of the surgical environment contains a portion of a non-biological foreign body, controlling the surgical laser to avoid interaction with the illuminated portion of the surgical environment.

2. The system of claim 1, wherein the operations further comprise:
   controlling the light source to illuminate a calibration object; and
   controlling the detector to obtain a calibration spectrum of light received by the detector from the calibration object being illuminated by the light source,
   wherein determining whether the illuminated portion of the surgical environment contains a portion of a non-biological foreign body based on the spectrographic content of the received light comprises comparing the spectrographic content of the received light to the calibration spectrum.

3. The system of claim 2, wherein determining whether the illuminated portion of the surgical environment contains a non-biological foreign body based on the spectrographic content of the received light comprises identifying a particular non-biological foreign body in the illuminated portion of the surgical environment based on the spectrographic content of the received light.

4. The system of claim 3, wherein the operations further comprise:
   classifying the particular non-biological foreign body as a particular type of non-biological foreign body based on the spectrographic content of the received light.

5. The system of claim 1, wherein the light source is a laser that emits light at a fixed wavelength.

6. The system of claim 5, wherein the fixed wavelength is an excitation wavelength of a fluorophore, wherein the fluorophore emits light at an emission wavelength in response to receiving light at the excitation wavelength, and wherein the spectrographic content of the light received from the illuminated portion of the surgical environment includes an intensity of received light at the emission wavelength.

7. The system of claim 1, further comprising:
an optical system that focuses the light from the light source to a spot within the surgical environment,
wherein controlling the light source to illuminate the portion of the surgical environment comprises controlling a location of the spot within the surgical environment.

8. The system of claim 1, further comprising:
an optical system that focuses light from the light source to a line within the surgical environment,
wherein controlling the light source to illuminate the portion of the surgical environment comprises controlling a location of the line within the surgical environment.

9. The system of claim 1, wherein the light source is a tunable laser controllable to emit light at any of a plurality of different wavelengths, wherein controlling the light source to illuminate the portion of the surgical environment comprises controlling the tunable laser to illuminate the portion of the surgical environment at each of the different wavelengths, and wherein the spectrographic content of the light received from the illuminated portion of the surgical environment includes a respective intensity of received light at each of the different wavelengths.

10. The system of claim 1, wherein the operations further comprise:
identifying a target tissue in the illuminated portion of the surgical environment based on the spectrographic content of the light received from the illuminated portion of the surgical environment; and
controlling the surgical laser to emit light to the target tissue in response to identifying the target tissue in the illuminated portion of the surgical environment.

11. The system of claim 1, wherein the operations further comprise:
controlling the light source to illuminate a plurality of additional portions of the surgical environment;
controlling the detector to obtain a respective spectrographic content of light received by the detector from each of the additional portions of the surgical environment illuminated by the light source; and
for each of the additional portions of the surgical environment, determining whether the additional portion of the surgical environment contains a portion of a non-biological foreign body based on the respective spectrographic content of the additional portion.

12. The system of claim 1, wherein the non-biological foreign body is a surgical instrument, fiducial, screw, staple, or suture.

13. The system of claim 1, wherein the non-biological foreign body is an object introduced by the surgical intervention.

* * * * *